(12) United States Patent
Misczynski et al.

(10) Patent No.: US 6,656,125 B2
(45) Date of Patent: Dec. 2, 2003

(54) SYSTEM AND PROCESS FOR ANALYZING A MEDICAL CONDITION OF A USER

(76) Inventors: Dale Julian Misczynski, 1800 Barton Creek Blvd., Austin, TX (US) 78735; Vladislav Bukhman, 419 First St., East Northport, NY (US) 11731; Sergii Tymoshok, 12 Priozernaja St., Apt. 109, Kiev (UA), 254211; Dmytro Tymoshok, 12 Priozernaja St., Apt. 109, Kiev (UA), 254211; Oleg Sergeevich Sychov, 30B Artema St., Apt. 2, Kiev (UA), 04053

(*) Notice: Subject to any disclaimer, the term of this patent is extended or adjusted under 35 U.S.C. 154(b) by 0 days.

(21) Appl. No.: 09/996,241

(22) Filed: Nov. 28, 2001

(65) Prior Publication Data

US 2002/0188214 A1 Dec. 12, 2002

Related U.S. Application Data

(60) Provisional application No. 60/295,194, filed on Jun. 1, 2001, and provisional application No. 60/339,875, filed on Oct. 31, 2001.

(51) Int. Cl.$^7$ .............................................. A61B 5/0452
(52) U.S. Cl. ....................................................... 600/508
(58) Field of Search ................................. 600/515–518, 600/508, 509; 128/923

(56) References Cited

U.S. PATENT DOCUMENTS 5,042,497 A * 8/1991 Shapland .................... 600/509
6,304,773 B1 * 10/2001 Taylor et al. ................ 600/515
6,411,840 B1 * 6/2002 Bardy .......................... 600/513

* cited by examiner

Primary Examiner—George R. Evanisko
(74) Attorney, Agent, or Firm—Winstead Sechrest & Minick P.C.

(57) ABSTRACT

A device and a process for analyzing a medical condition of a user. This device and process can also be used to predict a future abnormal medical condition of the user. The device includes a portable information-receiving device, an information processing device and a remote storage and processing device. These three devices may be in communication with each other via a wireless communication system. This device can include a GPS system for locating the user when the user is having an abnormal medical condition. The process is designed to take a digital signal from a plurality of ECG sensors on the portable information device and form a QRS wave. One or more points are extracted from this QRS wave are used to form a QRS complex wave. QRS complex waves are used to analyze the medical condition of the user. A plurality of parameters are calculated from these points on the QRS wave. If the medical condition of the user is in an abnormal range then an alarm will sound. However, if the user is not in an abnormal range, then the device may also predict the possibility of a future occurrence of an abnormal medical condition in the user.

29 Claims, 20 Drawing Sheets

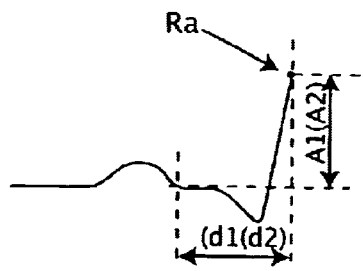 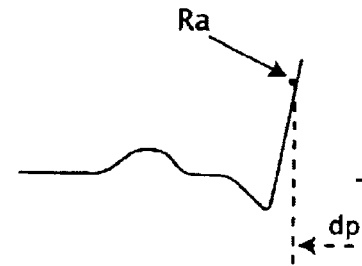 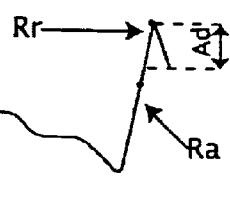
FIG. 9A  FIG. 9B  FIG. 9C
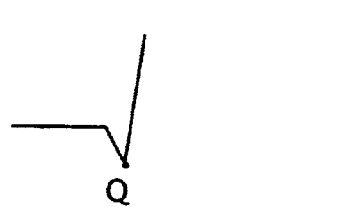 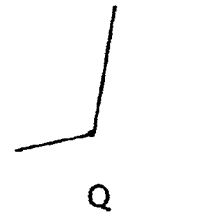 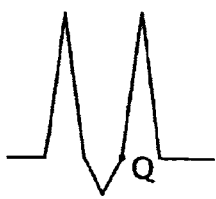
FIG. 10A  FIG. 10B  FIG. 10C
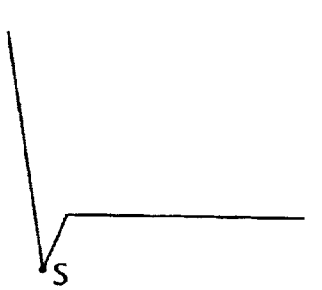 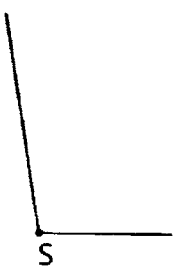 
FIG. 11A  FIG. 11B  FIG. 11C
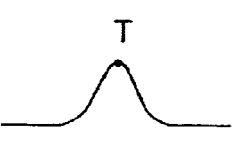 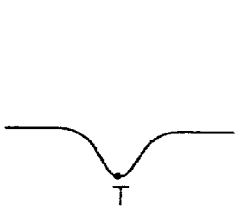 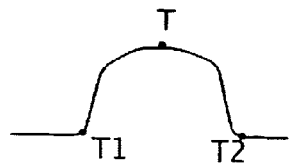
FIG. 12A  FIG. 12B  FIG. 12C

| Parametric value | Description |
|---|---|
| Pulse rate | Defined as average value of R-R Interval of 4 last R-R Intervals per 1 minute |
| Immediate alteration of pulse rate | Defined as difference between Pulse Rate calculated for the last 4 R-R Intervals and Pulse Rate calculated for previous 4 R-R Intervals (i = N-7,..,N-4): $P_a = P_N - P_{N-3}$ |
| RR-Interval | Defined as a distance between 2 consecutive R-peak (ms) |
| Premature beats | The number of extrasystoles within last 10 seconds. |
| Group of premature beats | The number of consecutive extrasystoles |
| The atrial fibrillation-flutter | $F = (F1 + F2) * X$ (%), where: F1 – Extrasystole factor and F2 – Variability factor for the last 15 R-R intervals |
| ST-Segment depression/elevation | Defined as a distance (mm) between point K and isoline of QRS-complex. Its value is averaged for last 10 QRS-complexes |
| T-wave inversion | Inversion of current T-peak is identified within localization of point T. Cardiac event "T-wave Inversion" is occurred if 4 consecutive inverse T-peak are received |
| Width of Q-wave | Distance between point I and Q' in ms |
| Ratio of amplitude Q-wave to amplitude R-wave | $A_{QR} = \dfrac{A_I \ A_Q}{A_R \ A_I}$ 100%, $A_{QR}$ value is averaged for the last 5 QRS-complexes |
| Amplitude of R-wave | Defined as difference between absolute values of point R amplitude and point I amplitude: $A_{Rd} = (A_R \ A_I)\ 0.2$ (mm) $A_{Rd}$ value is averaged for the last 5 QRS-complexes |
| Width of QT-interval | Defined as distance (ms) between point I of beginning of Q-peak and point T2-peak of the end of T-peak |
| Width of QRS-complex | Defined as the distance (ms) between point I and point J |
| Width of PQ-interval | $W_{PQ}$ is defined as the distance (ms) between point P1 of beginning of P-peak and point I. $W_{PQ}$ value is averaged for the last 5 QRS-complexes |
| Standard deviation of the average normal-to-normal R-R intervals | Sinus node depolarization calculated over a period of 5 min |

FIG. 14

Typical threshold parameters values

| Warning | Alarm | Description |
|---|---|---|
| $W_1$ | $A_1$ | Pulse rate less than 50/40 bpm (during 4 QRS complexes) |
| $W_2$ | $A_2$ | Pulse rate more than 140/160 bpm (during 4 QRS complexes) |
|  | $A_3$ | Immediate alteration of pulse rate up, more than 40 bpm (during 4 QRS complexes) |
|  | $A_4$ | Immediate alteration of pulse rate down, more than 40 bpm (during 4 QRS complexes) |
|  | $A_5$ | R-R interval more than 2.5 sec |
|  | $A_6$ | Premature beats, repeated more then 1 in 10 sec |
|  | $A_7$ | 2 consecutive premature beats |
| $W_8$ | $A_8$ | The atrial fibrillation-flutter > 20/30 % |
| $W_9$ | $A_9$ | ST-segment depression > 1.0/1.5 mm, measured at 80 ms from J-point |
| $W_{10}$ | $A_{10}$ | ST-segment elevation > 1.5/2.0 mm, measured at 80 ms from J-point |
|  | $A_{11}$ | T wave inversion = 1 |
| $W_{12}$ | $A_{12}$ | Increase of Q wave > 30/40 ms |
| $W_{13}$ | $A_{13}$ | Increase of Q/R amplitude ratio > 20/30 % |
| $W_{14}$ | $A_{14}$ | Decreases of R-wave amplitude > 30/50 % |
| $W_{15}$ | $A_{15}$ | Increase of QT interval > 450/500 ms |
|  | $A_{16}$ | Sudden increase of QT interval > 30 % from preceded |
| $W_{17}$ | $A_{17}$ | Increase of QRS duration > 110/120 ms |
| $W_{18}$ | $A_{18}$ | Increase of PQ interval > 180/200 ms |
| GE | $A_7$ | Consecutive premature beats > 2 |
| $ST_{W9}$ | $ST_{A9}$ | ST-segment depression > 1.5/2.0 mm, measured at 80 ms from J-point |
| $ST_{W10}$ | $ST_{A10}$ | ST-segment elevation > 2.0/2.5 mm, measured at 80 ms from J-point |
| $W_G$ | $A_G$ | Integrated Relative Risk of SCD or development of Myocardial Infarction > 1.8/2.5 |

FIG. 16A

Pulse-metric parameters

| Warning | Alarm | Description |
|---|---|---|
| $W_1$ | $A_1$ | Pulse rate less than $A_1(W_1)$ bpm (during 4 QRS complexes) |
| $W_2$ | $A_2$ | Pulse rate more than $A_2(W_2)$ bpm (during 4 QRS complexes) |
|  | $A_3$ | Immediate alteration of pulse rate up, more than $A_3$ bpm (during 4 QRS complexes) |
|  | $A_4$ | Immediate alteration of pulse rate down, more than $A_4$ bpm (during 4 QRS complexes) |
|  | $A_5$ | R-R interval more than $A_5$ sec |
|  | $A_6$ | Premature beats, repeated more then $A_6$ in 10 sec |
|  | $A_7$ | $A_7$ consecutive premature beats |
| $W_8$ | $A_8$ | The atrial fibrillation-flutter > $A_8(W_8)$ % |

FIG. 16B

QRS parameters

| Warning | Alarm | Description |
|---|---|---|
| $W_9$ | $A_9$ | ST-segment depression > $A_9(W_9)$ mm, measured at 80 ms from J-point |
| $W_{10}$ | $A_{10}$ | ST-segment elevation > $A_{10}(W_{10})$ mm, measured at 80 ms from J-point |
|  | $A_{11}$ | T wave inversion = $A_{11}$ |
| $W_{12}$ | $A_{12}$ | Increase of Q wave > $A_{12}(W_{12})$ ms |
| $W_{13}$ | $A_{13}$ | Increase of Q/R amplitude ratio > $A_{13}(W_{13})$ % |
| $W_{14}$ | $A_{14}$ | Decreases of R-wave amplitude > $A_{14}(W_{14})$ % |
| $W_{15}$ | $A_{15}$ | Increase of QT interval > $A_{15}(W_{15})$ ms |
|  | $A_{16}$ | Sudden Increase of QT interval > $A_{16}$ % from preceded |
| $W_{17}$ | $A_{17}$ | Increase of QRS duration > $A_{17}(W_{17})$ ms |
| $W_{18}$ | $A_{18}$ | Increase of PQ interval > $A_{18}(W_{18})$ ms |

FIG. 16C

Extended pulse-metric parameters

| Warning | Alarm | Description |
|---|---|---|
| GE | $_{A7}$ | Consecutive premature beats > $GE_{A7}$ |

FIG. 16D

Extended QRS parameters

| Warning | Alarm | Description |
|---|---|---|
| $ST_{W9}$ | $ST_{A9}$ | ST-segment depression > $ST_{A9}$ mm, measured at 80 ms from J-point |
| $ST_{W10}$ | $ST_{A10}$ | ST-segment elevation > $ST_{A10}$ mm, measured at 80 ms from J-point |

FIG. 16E

Integrated parameters

| Warning | Alarm | Description |
|---|---|---|
| $W_G$ | $A_G$ | Integrated Relative Risk of SCD or development of Myocardial Infarction > $A_G$ |

FIG. 16F

SYSTEM AND PROCESS FOR ANALYZING A MEDICAL CONDITION OF A USER

CROSS REFERENCE TO RELATED APPLICATIONS

This patent application is based upon Provisional Patent Application Ser. No. 60/295,194 filed on Jun. 1, 2001 and a second provisional Patent Application, Ser. No. 60/339,875, filed on Oct. 31, 2001 wherein priority is claimed under 35 U.S.C. § 119e.

BACKGROUND

Portable medical information analyzers are known in the art. For example, medical information analyzers are disclosed in the following U.S. Pat. Nos. 6,206,829; 6,171,264; 6,171,237; 6,162,180; 6,160,478; 6,149,585; 6,108,578; 6,102,856; 6,100,806; 6,093,146; 6,072,396; 6,067,466; 6,049,794; 6,047,203; 6,039,688; 6,011,989; 5,971,921; 5,959,529; 5,942,986; 5,941,829; 5,931,791; 5,921,938; 5,919,141; 5,878,746; 5,876,351; 5,873,369; 5,855,550; 5,840,020; 5,782,878; 5,772,586; 5,735,285; 5,704,364; 5,678,562; 5,564,429; 5,544,661; 4,909,260, incorporated herein by reference.

In addition, the following references are also known in the art: Russian Application No. 98106704/13 M.C. A615b5/02, A61B5/0452 published on Oct. 2, 2000. In addition Russian application No. 98103717/14 M. cl. A61B5/0452 published on Oct. 1, 2000; Russian Patent Application No. 97113351/14 M. cl. A61B5/02 published on Feb. 6, 1999; and finally, Russian Patent Application No. 93016579.

All of these references have one or more significant disadvantages. First, there are few parameters being analyzed in that only one parameter may be analyzed at one time instead of multiple parameters. Second, there is no real time complex approach to a patient's complex present state evaluation because one or more of the above references require the direct participation of an expert evaluating the parameters. Third, many of the devices described by the prior art require the patient to be located adjacent to the evaluation device. Since evaluation devices may be the size of a personal computer, this limits the availability for patients to use these monitoring devices.

In addition, in all of the previous models, the ECG waves were read directly and then analyzed. In the present invention a few preliminary points are analyzed first and then the ECG information is reconstructed in the form of a QRS wave. In addition, this invention involves a predictive model that uses one or more parameters derived from this QRS wave to determine the possibility of the user experiencing an abnormal medical occurrence.

Thus, in the past, patients may have been reluctant to use these medical information analyzers because they were too large and cumbersome. Furthermore, doctors or other medical professionals may have been reluctant to prescribe the use of these portable medical information analyzers because they might provide insufficient, or incorrect medical information.

For example, this medical information analyzer could be used to detect heart arrhythmias. Arrhythmias are a disturbance in the rate or rhythm of the heartbeat. Various arrhythmias can be symptoms of serious heart disorders; however, they are usually of no medical significance except in the presence of additional symptoms.

The heart's rhythm is controlled by an electrical impulse that is generated from a clump of tissue on the right atrium called the sinoatrial node, often referred to as the heart's natural pacemaker. It travels to a second clump of tissue called the atrioventricular node and then to the ventricles. Bradycardia, or slow heartbeat, is often present in athletes. It may, however, indicate conduction problems, especially in older people. In one type of bradycardia, called sinoatrial or atrioventricular block, or heart block, rhythm can be maintained by implanted electrodes that act as artificial pacemakers. Drugs, caffeine, anemia, shock, and emotional upset can precipitate tachycardia or heartbeat faster than 100 beats per minute in the adult. It may also be a sign of over activity of the thyroid gland or underlying disease.

Flutters, and the even faster fibrillations, are rapid, uncoordinated contractions of the atrial or ventricular muscles that usually accompany heart disorders. Atrial fibrillation may be idiopathic, the result of rheumatic mitral valve disease (see rheumatic fever) in young people or hypertensive heart disease (see hypertension) and arteriosclerotic heart diseases (see arteriosclerosis) in older people. It may result in a rapid pulse rate and may be associated with thrombus formation in the atria and a risk of embolization to the brain (stroke) or other organs.

Atrial fibrillation is often treated with digitalis. Ventricular fibrillation is a sign of the terminal stage of heart failure and is usually fatal unless defibrillation is achieved by immediate direct-current defibrillation. Some tachycardias can be managed by the implantation in the upper chest of small defibrillators that sense dangerous fibrillations and administer an electric shock to the heart to restore normal rhythm. *The Columbia Encyclopedia, Sixth Edition.* 2001.

SUMMARY OF THE INVENTION

These problems are overcome by providing a new system and process for evaluating a medical condition of a patient by providing an improved portable medical information analyzer and an improved central information-processing device in one system.

One object of this invention is to provide a process for calculating a QRS line based upon a limited number of preliminary points or indicia taken from an individual.

Another object of the invention is to provide an accurate estimator of the future probability of an abnormal medical condition by using a patient's ECG reading in a customized algorithm to determine the patient's risk for incurring an abnormal medical condition.

Still another object of the invention is to provide a portable information device that is designed to receive signals from a user wherein these signals are then analyzed as described in the first two objects of the invention.

The invention relates to a portable medical information-analyzing device that may comprise at least one sensor for extracting medical information from a user. The user could either be a person or an animal.

This device also comprises at least one transceiver for transmitting this medical information from the user and at least one external interface to control external equipment that relates to the user. In addition, the transceiver is designed to receive information from the information-processing device. Thus, this portable information device sends this information onto an information-processing device and receives information from it. The information-processing device comprises at least one transceiver for receiving and transmitting the medical information from and to the portable information device.

There is also at least one medical information analyzer, which calculates a series of medical-based parameters from this medical information. The system also includes at least one data store in communication with the medical information analyzer. The data store stores a set of predetermined data on these medical-based parameters. There is also at least one parameter analyzer, which compares a set of predetermined data in the data store with the medical-based parameters calculated from this medical information.

Once this information has been determined, it is sent to an abnormality identifier, which then determines whether these parameters are out of line with the present set of parameters, and determines a risk assessment, which is used to determine the type of alarm used to signal the user. Finally, there is also an alarm, which sends an alarm signal to the user when the medical based parameter analyzer determines a medical abnormality based upon a comparison of the set of predetermined data with the medical information.

The invention also relates to a process for analyzing the medical condition of the user. In this case, the process can either operate using the device described above or use another type device such as a personal computer. The process includes the first step of gathering medical information from a user. Next, the process involves sending this information to a medical information analyzer. The medical information analyzer extracts particular points on a QRS wave out of the ECG information, analyzes this information, and then reconstructs the QRS wave so that it does not have any noise. Next, this analyzer breaks this information down into a plurality of discrete parameters. These parameters are: 1) pulse rate; 2) immediate alteration of pulse rate; 3) R—R interval; 4) premature beats; 5) group of premature beats; 6) atrial fibrillation flutter; 7) ST-segment depression/elevation; 8) T-wave inversion; 9) width of Q-wave; 10) Ratio of Amplitude of Q-wave to Amplitude of R-wave; 11) Amplitude of R wave; 12) Width of QT-interval; 13) Width of QRS complex; 14) Width of PQ interval; and 15) Standard Deviation of the average normal-to-normal R—R intervals. These parameters are then compared with a set of pre-set parameters to determine whether a user is experiencing abnormal symptoms. Depending upon the value of the calculated parameter, the parameter definition, and the risk analysis, an alarm may be activated to signal the user that the user has entered an abnormal medical condition.

To predict whether the user will experience an abnormal medical condition, such as the complex risk of sudden cardiac death, a plurality of parameters are compiled in a formula. These parameters relate to the previously mentioned parameters in that these parameters involve the ST init., which is the ST segment level before the observation begins; ST meas., which is the ST segment level at the current movement; ST thresh., which is the ST segment threshold at normal levels; QT meas. which is the QT interval duration at the current moment; QT norm., which is the QT interval normal duration.

Thus, this formula builds upon the parameters that are calculated when determining whether the user is experiencing an abnormal medical condition.

In addition, this type of risk can be adjusted for each user so that the system learns the boundaries for each user. Ultimately, once the abnormal medical condition has been determined, the system determines which alarm to activate to warn the user. This information in the form of the alarm is then communicated to the portable information device to control external equipment or stimuli at the user based upon the medical and environmental information.

BRIEF DESCRIPTION OF THE DRAWINGS

Other objects and features of the present invention will become apparent from the following detailed description considered in connection with the accompanying drawings, which disclose several embodiments of the present invention. It should be understood, however, that the drawings are designed for the purpose of illustration only and not as a definition of the limits of the invention.

In the drawings wherein similar reference characters denote similar elements throughout the several views:

FIG. 9A is a graph showing a close up view of a QRS complex showing where point R has been preliminarily identified;

FIG. 9B is a graph showing a close up view of a QRS complex showing the refinement of point R;

FIG. 9C is a graph showing a close up view of a QRS complex showing where real point R has been defined;

FIG. 10A is a close up view of a QRS complex showing a normal Q wave;

FIG. 10B is a close up view of a QRS complex showing a depressed Q wave;

FIG. 10C is a close up view of a QRS complex showing a Q-wave typical for a group of extrasystoles;

FIG. 11A is a close up view of a QRS complex showing a normal S-wave;

FIG. 11B is a close up view of a QRS complex showing a depressed S-wave;

FIG. 11C is a close up view of a QRS complex showing a S-wave typical for a group of extrasystoles;

FIG. 12A is a close up view of a QRS complex showing a normal T wave;

FIG. 12B is a close up view of a QRS complex showing an inverse T wave;

FIG. 12C is a close up view of a QRS complex showing a normal T wave with a weakly expressed maximum;

FIG. 14 is a table representing the plurality of parameters and their definitions;

FIG. 16 is a table showing a process to determine whether to trigger an alarm/warning regarding the information processed in FIG. 15;

DETAILED DESCRIPTION OF THE PREFERRED EMBODIMENT

Referring in detail to the drawings, FIGS. 1A–5 show the different embodiments of a device for determining an abnormal medical condition while FIGS. 6–19 show the process for determining and predicting an abnormal medical condition. The process may be preferably carried out via the device but the process according to the invention is not restricted to this device according to the invention.

Figure 1A:
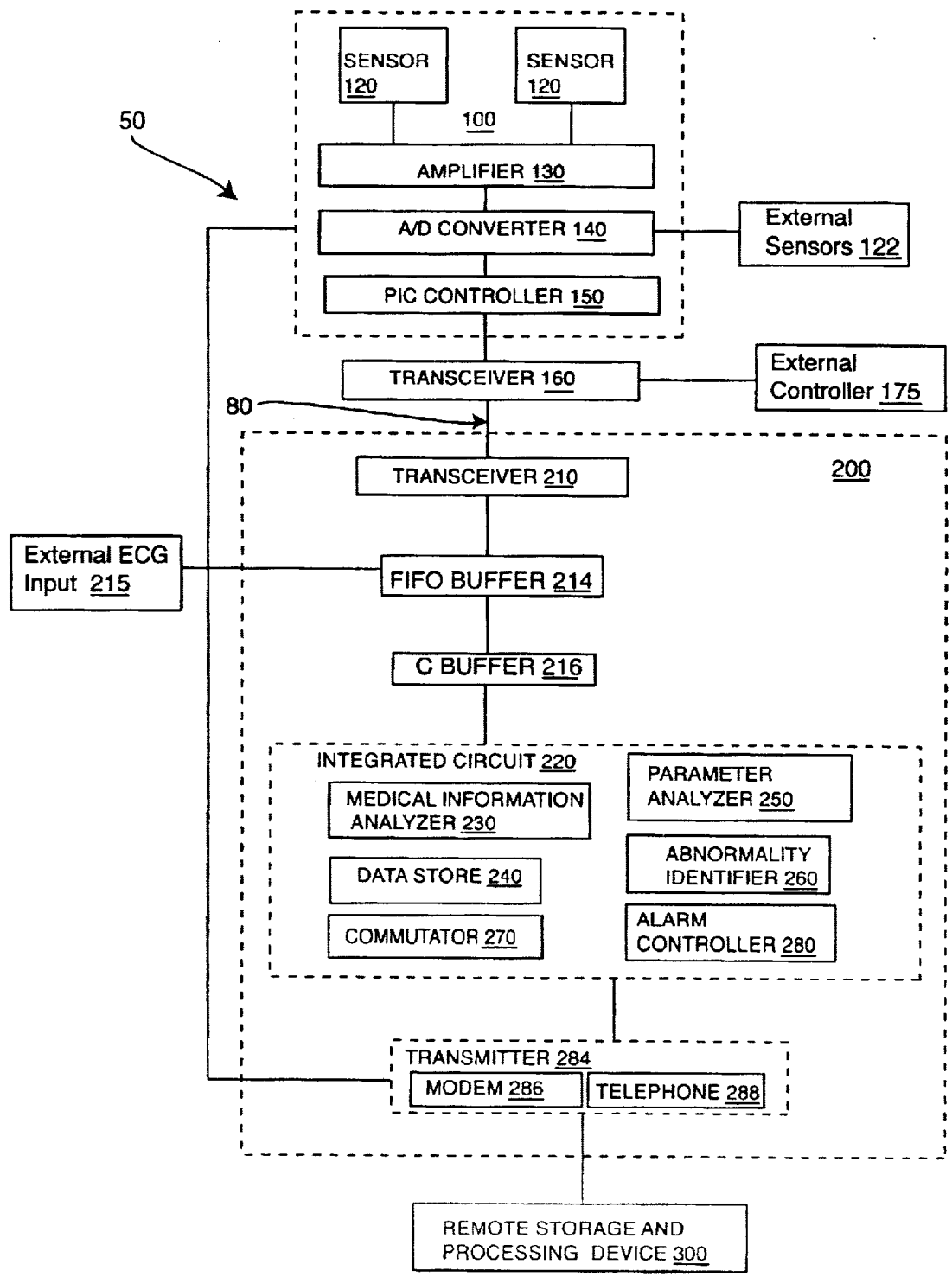
FIG. 1A is a schematic block diagram of the system for processing and analyzing information related to the health of a user.
Figure 1B:
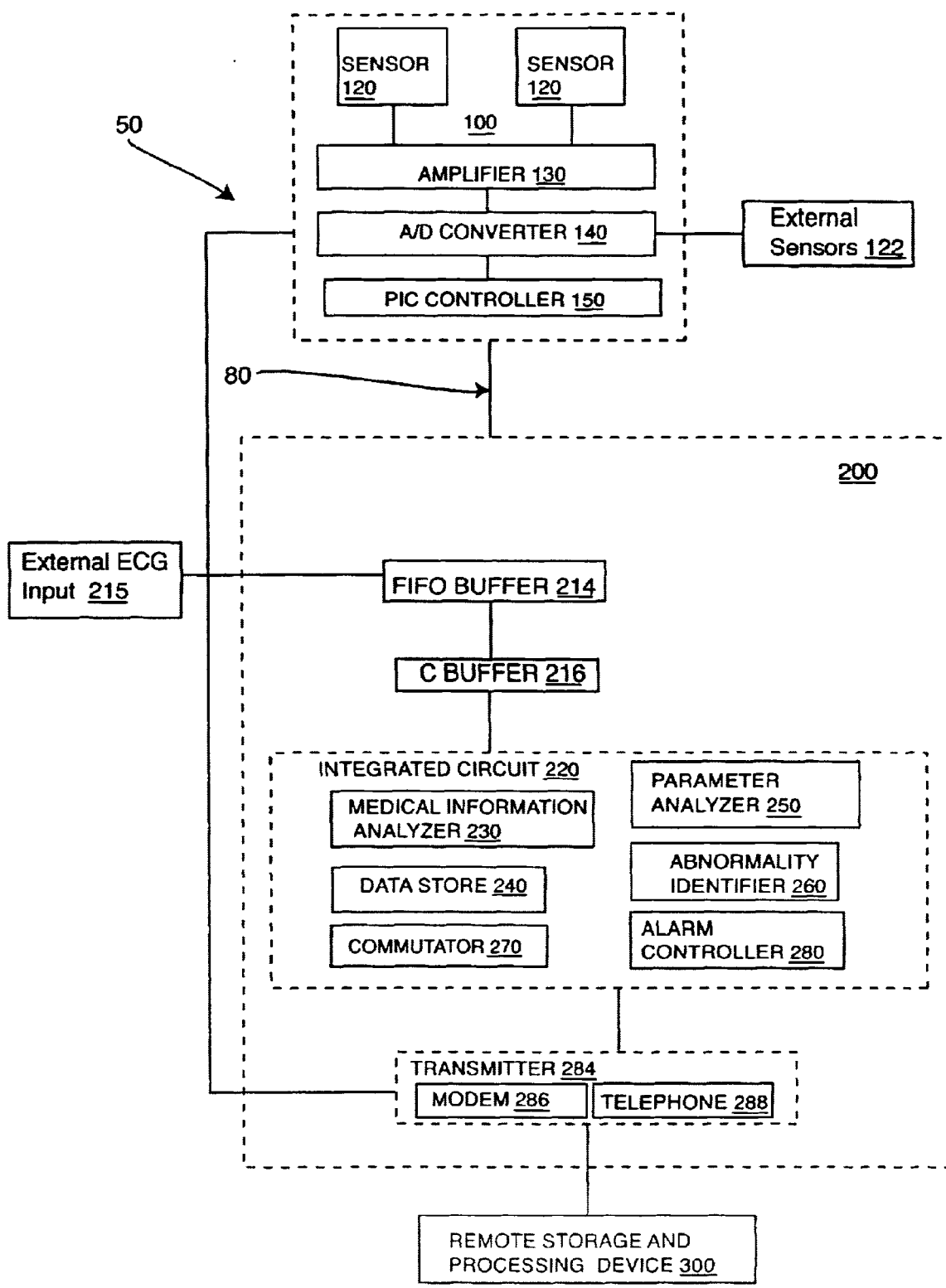
FIG. 1B is a second embodiment of the schematic block diagram in FIG. 1A.

FIGS. 1A and 1B are schematic block diagrams of the system 50 for processing and analyzing information related to the health of a user. System 50 includes a portable information device 100 a central information processing device 200 and a central information storage device 300 all in communication with each other. As shown in FIG. 1A there is a wireless connection as shown that can include communication via Bluetooth™ technology, radio frequency, infrared communication, or any other wireless connection known in the art. FIG. 1B shows a bi-directional communication between these devices can be in the form of a hard-wired connection or through wireless communication. The hard-wired connection is shown through lines 80 showing the optional use of communication lines 80 such as Ethernet or other type cabling known in the art.

Essentially, portable information device 100 reads medical information from a user such as a human being or an animal. This information, which is in the form of packaged digitalized bioelectric signals, is then communicated to information processing device 200. Once this information has been received it is entered into a FIFO buffer 214 and then a C buffer 216 before it is analyzed. Information processing device 200 analyzes this information and then determines whether the user is experiencing any abnormal symptoms. Next, information processing device 200 either sends an alarm or control signal to the user, portable information device 100, or to a medical professional if the user is experiencing any abnormal symptoms. Information-processing device 200 can also signal to portable information device 100 to cause various actions to the user, or the users' environment.

Figure 2:
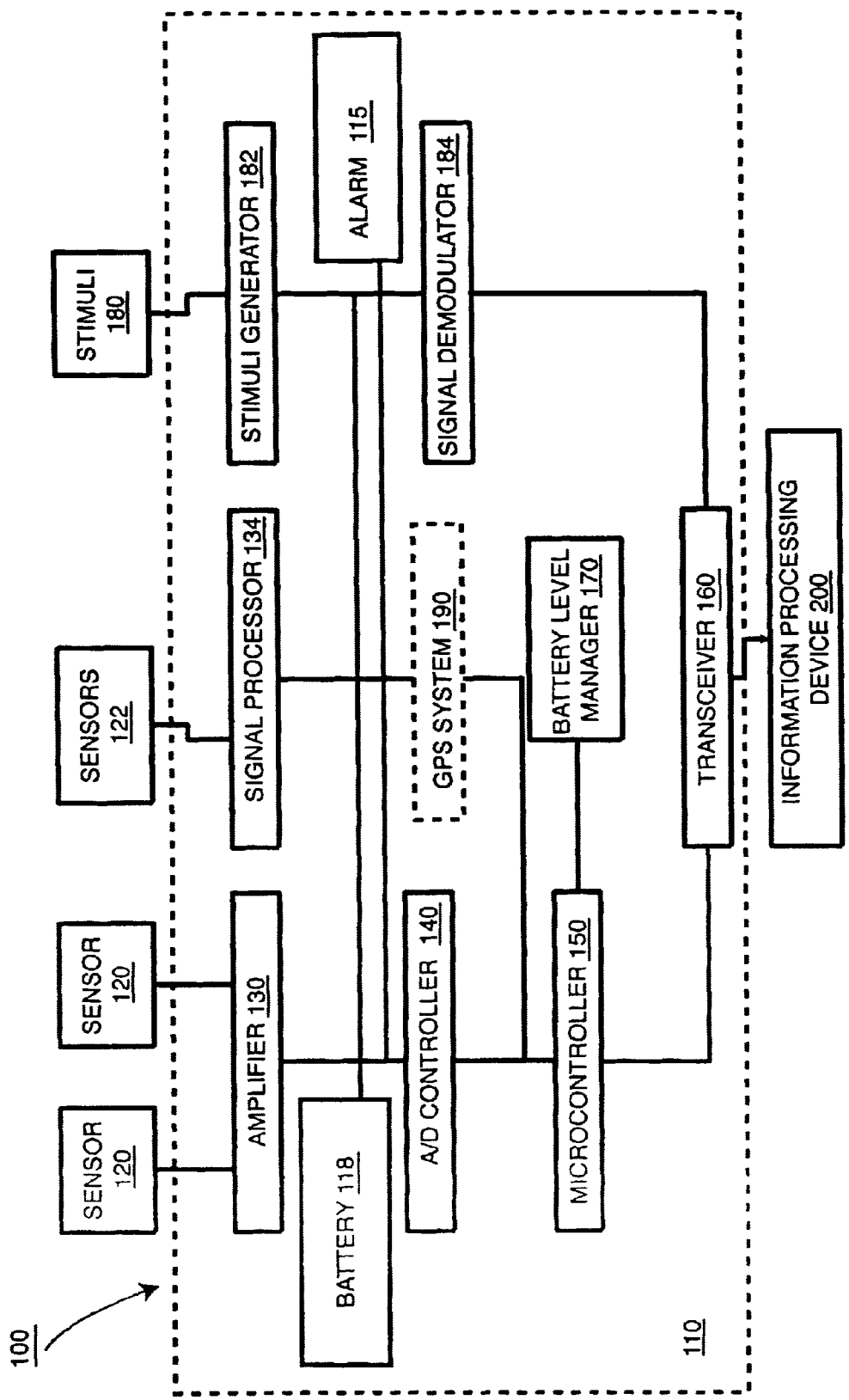
FIG. 2 is a schematic block diagram of a more detailed view of a portable information device shown in FIGS. 1A and 1B.

FIG. 2 is a schematic block diagram of a more detailed view of a portable information device 100 shown in FIGS. 1A and 1B. Portable information device 100 includes a housing 110 which can be in the form of a belt that wraps around the user, a garment, or other housing that contains the sensors, or the sensors may be implanted within the body. Housing 110 contains an alarm 115 to alarm the user when the user has an abnormal medical condition. In addition, included with this housing is a battery pack or power supply 118 that powers the components in the housing and the sensors and stimuli outside the housing. On the outside face of housing 110 is a plurality of sensors 120 that read medical information from the user in the form of an analog signal. Other remote sensors 122 (See FIG. 1A) are disposed outside housing 110 and maybe in the form of patches on the user, or may be embedded or implanted. These plurality of sensors are in communication with an amplifier 130 or a microcontroller 150 via a signal processor 134. Amplifier 130 amplifies the analog signal received from sensors 120 so that this information can be read by analog to digital (A/D) converter 140. Analog to digital converter 140 converts the analog information into digital information. In addition, signal processor 134 processes signals from sensors 122 so that these signals can then be sent to microcontroller 150.

A battery level manager 170 is coupled to microcontroller 150 to control the energy use in that device. In addition, also coupled to the device is a stimuli reader 180, a stimuli generator 182, and a signal demodulator 184 all coupled to transceiver 160. There is also a GPS tracking system 190, which is shown in dashed lines and coupled to processor 150. The dashed lines are present because this device can be either coupled to portable information device 100, or to information processing device 200 as GPS system 290. In addition, an external controller 175 as shown in FIG. 1A can be in communication with transceiver 160 to instruct stimuli generator (See FIG. 2) to create a stimuli action on a user such as an injection of medication or shock therapy.

Sensors 122 monitor other information concerning the user. Several of the sensors may read information concerning the user's environment, such as temperature, humidity and location (GPS). The information from these sensors is sent to signal processor 134, which feeds the information to the microcontroller 150. There is also the capability to receive information from the information-processing device 200. This information is decoded in signal demodulator 184 and is used to control various external stimuli such as, but not limited to, the dispensing of various pharmaceuticals, electrical stimulus, auditory and visual stimulus, and other sensory stimulus.

The digital information is then sent to microcontroller 150 which can be in the form of a controller that creates a series of data packets, which contains information about the ECG fragments. This information is then sent through transceiver 160 which can either be a wire-based transceiver or a wireless transceiver such as a Bluetooth™ transceiver or an infrared transceiver. If transceiver 160 is wire based, then the information flows through lines 80 (FIG. 1B) and on to information processing device 200.

The portable information device 100 also receives signals from the information-processing device 200. These signals may be commands associated with the information being sent from the portable information device or the information may be independent.

Figure 3:
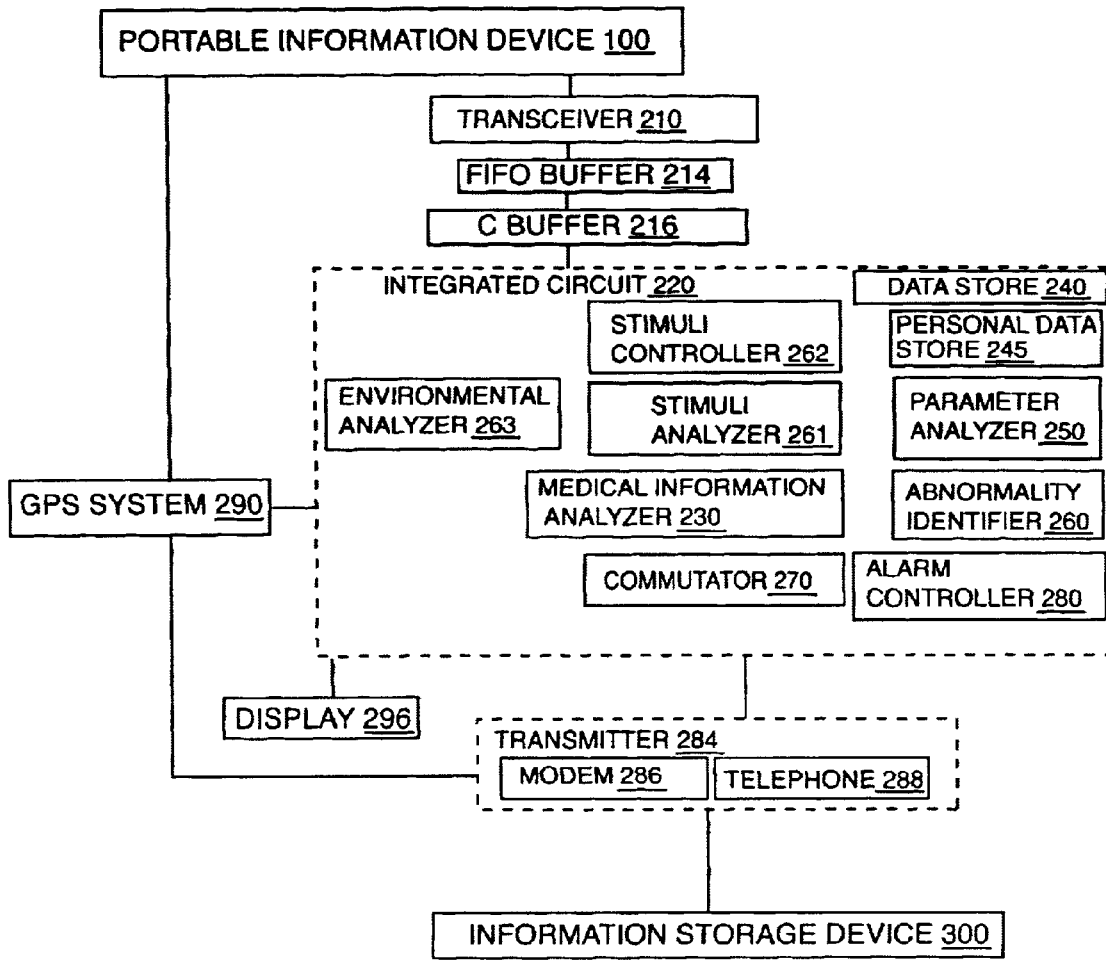
FIG. 3 is a schematic block diagram of a first embodiment of the information-processing device shown in FIG. 1A.

FIG. 3 is a schematic block diagram of a first embodiment of information-processing device 200 substantially shown in FIG. 1A. Information processing device 200 can be in the form of a PC, or in the form of a portable device that can attach to a user or may be in other forms. Information processing device 200 can be powered either by a battery or an A/C power supply (not shown). Information processing device 200 includes a bi-directional wireless or wire based transceiver 210 that sends and receives information either through a wire based system such as a LAN or a wireless system such as Bluetooth™ technology, infrared or RF frequency transmissions. If information processing device 200 is in the form of a personal computer, then the method for communication will most likely be wireless. However, if information processing device 200 is in the form of a portable device then the method for communication could be either wire or wireless based.

With this first embodiment, there are a series of elements all stored on a single programmable integrated circuit or IC 220. Because an integrated circuit or IC 220 is used, these elements are distinguished primarily by the software that is used on the circuit. IC 220 includes one or more medical information analyzers 230. Medical information analyzer 230 first extracts a plurality of points taken from ECG waves. Next analyzer 230 reconstructs a QRS wave using these points. Next, medical information analyzer calculates a series of medical-based parameters from the medical information received by transceiver 210. These medical-based parameters are calculated using a series of formulas based upon points plotted on a graph shown in FIG. 8A.

In addition, disposed on IC 220 is at least one data store 240, which is in communication with medical information analyzer 230. Data store 240 stores a set of predetermined data based on the set of medical-based parameters. This predetermined data can be adjusted or adapted to change once new information enters the system. The adaptive changes can be based upon a single user, or a population of users. The predetermined data is a result of a series of tests performed on users that experience medical abnormalities such as a myocardial infarction or heart attack.

In addition, on IC 220 is at least one medical-based parameter analyzer 250, which compares either the set of predetermined data in data store 240 or personalized predetermined data in personal data store 245 with the medical-based parameters, calculated from the medical information.

Parameter analyzer 250 collects and analyzes data form a history file and a cardiac events log file. Parameter analyzer 250 determines the new ranges of threshold parameters based demographic data, history file, and log file of cardiac events. Parameter analyzer 250 then presets the previous baseline parameters based upon the results of the adaptive analyzer to personal data store 245.

If parameter analyzer 250 finds data that is consistently in an abnormal range, then an abnormality identifier 260 sends information to an alarm controller 280. Alarm controller 280 sends this information to a transceiver 284 that includes a modem 286 and a telephone line 288 or to an alarm 294. Modem 286 sends these readings along with an analysis of these readings either to a doctor or on to a user such as a patient in the form of an alarm or warning wherein this alarm or warning is signaled on alarm 115.

The alarm controller can also determine that certain actions may be required at the user. In which case, information concerning the alarm and required action is communicated to the portable information device on the patient where external devices may be used to administer medicine or external stimuli.

In addition, there is also an external stimuli analyzer 261 and an environmental analyzer 263 also disposed within IC 220. External stimuli analyzer 261 receives information from abnormality identifier 260 and determines whether to introduce an external stimuli to the user through stimuli generator 182 via transceiver 160. In most cases alarm controller 280 will simultaneously send an alarm to the user to warn the user of his or her abnormal medical condition.

Environmental analyzer 263 receives information from portable information device 100 regarding the user's environment such as temperature, and humidity. Environmental analyzer will analyze this information to warn the user to seek an alternative environment if the current environment is harmful to the user. Essentially, environmental analyzer 263, which is coupled to abnormality identifier 260 and alarm controller 280, signals alarm controller 280 to send out an alarm when the user's environment has exceeded recommended levels. This signal is sent through transceiver 210 to transceiver 160 to warn the user. A GPS system 290, which may be optional, can be coupled to information processing device 200. This GPS system 290 is useful if information processing device 290 is positioned on the body of a user or adjacent to a user. In that way, the GPS position identified by GPS system 290, would be the same or substantially similar to the GPS position of the user.

There is also a display and input output device 296 that connects to information processing device 200 that allows a user to see information that is processed within information processing device 200. Display 296 can be either a standard monitor coupled to a personal computer or a customized display for a portable version of information processing device 200.

Besides receiving information from the portable information device 100, information developed by other forms of cardiac monitoring equipment can also be read and processed by the system. Information sources may be, but not limited to, Holter monitors, card loop monitors, and other similar sources.

In addition to the ECG monitoring and analysis functions, the system also analyzes other health and environmental data coming from external sensors. The data is analyzed in conjunction with outputs of Abnormality identifier 260 or analyzed separately in external stimuli analyzer 261. Data is also analyzed in environmental analyzer 263. The environmental analyzer 263 compares the environmental data received from the portable information device 100 and compares the received conditions to preset upper and lower bounds for each environmental condition. Exceeding the upper and lower bound will generate a signal to the abnormality identifier 260. The output of the combined analysis will vary depending on the individual patient condition. There may be a set of preset levels against which the analysis is conditioned, or the upper and lower constraints may be set according to the individual user conditions.

If the stimuli analyzer determines that an external stimuli response is required, then the stimuli controller 262 sends a signal to the transceiver 210. In this step, the stimuli signals are sent to the transceiver 160, which sends the data to the external controller.

Figure 4:
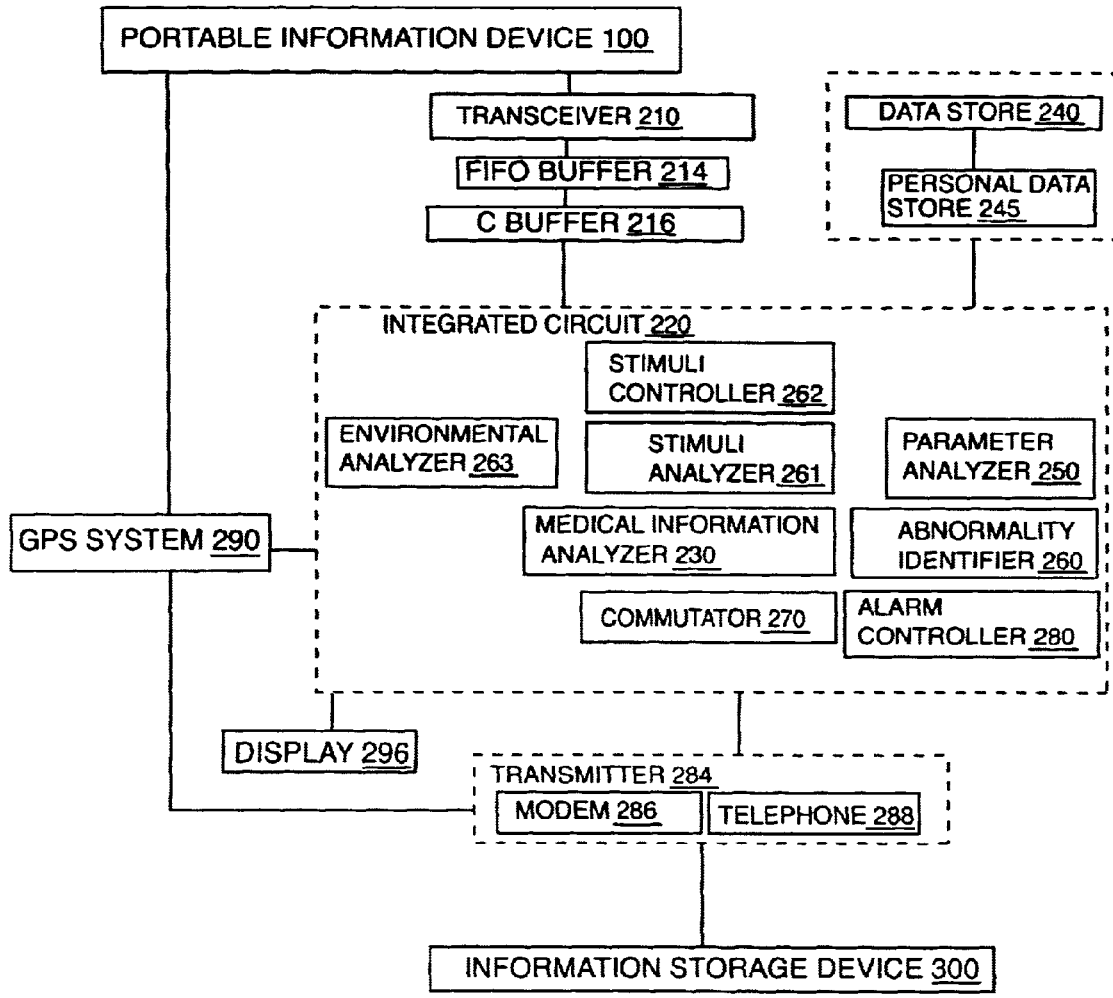
FIG. 4 is a schematic block diagram of a second embodiment of the information-processing device shown in FIG. 1A.

FIG. 4 is a schematic block diagram of a second embodiment of the information-processing device shown in FIG. 1. In this embodiment, medical information analyzer 230, medical-based parameter analyzer 250, and abnormality identifier 260, external stimuli analyzer 261, external stimuli controller 262, environmental analyzer 263, commutator 270 and alarm controller 280 are all disposed on a single integrated circuit (IC) circuit 221. Data store 240, and personal data store 245, are coupled to (IC) 221 as physically separate elements. However, these physically separate elements still work in a manner similar to the components in (IC) 220 to produce substantially the same result.

Figure 5:
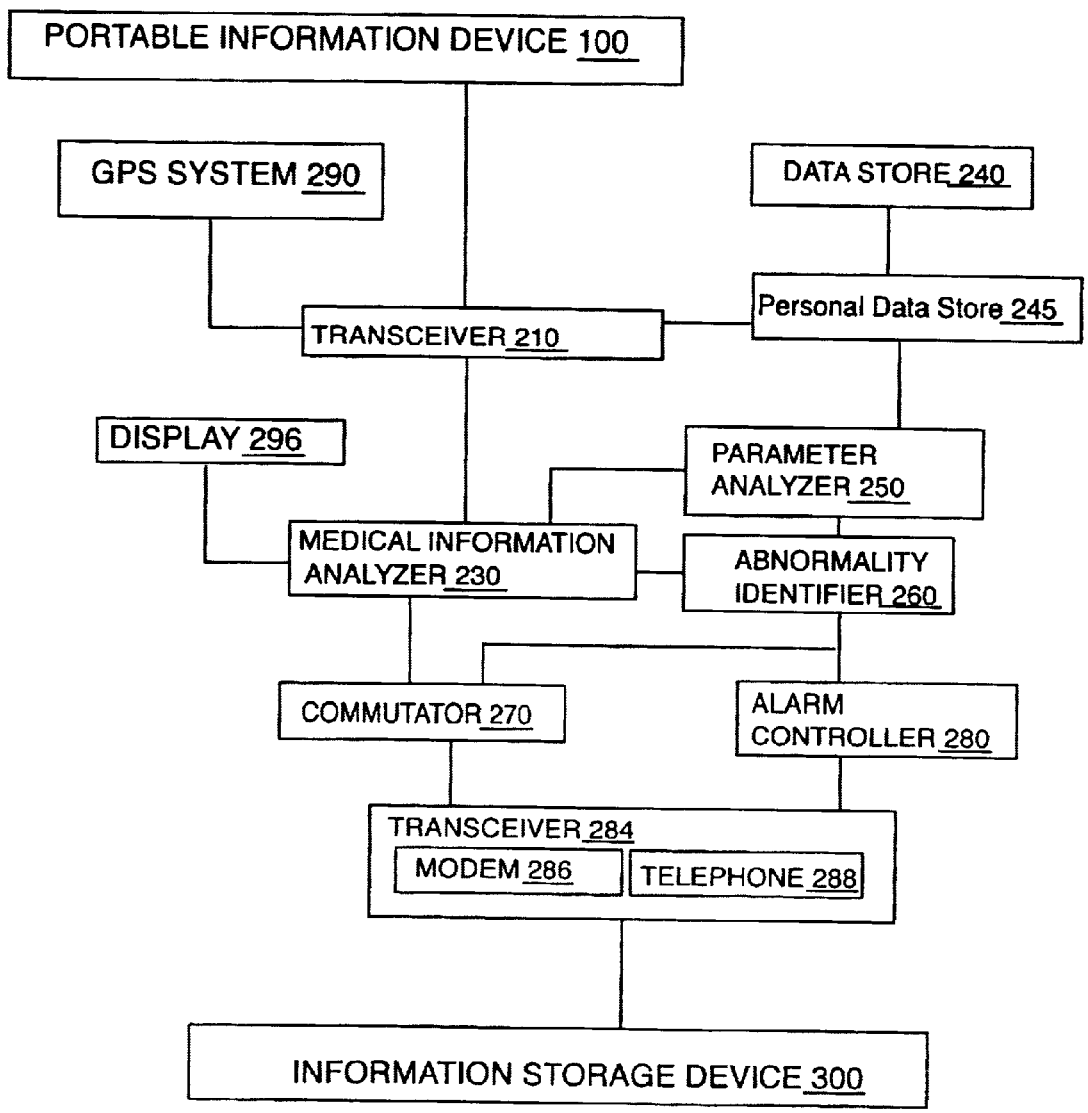
FIG. 5 is a schematic block diagram of a third embodiment of the information-processing device shown in FIG. 1A.

FIG. 5 is a schematic block diagram of a third embodiment of the information-processing device shown in FIG. 1. In this embodiment all of the components originally on IC circuit 220, are now separate elements coupled to each other and in communication with each other. These separate elements, include medical information analyzer 230, data store 240, medical parameter analyzer 250, abnormality identifier 260, commutator 270, and alarm controller 280.

Not included in this design are external stimuli analyzer 261, stimuli controller 262 and environmental analyzer 263. All other elements such as transceiver 284 are also connected to these components as separate elements. In addition, in this embodiment, GPS system 290 is coupled to portable information device 100. With this design, portable information device 100 can be located in a remote location, away from information processing device 200 and still deliver the location of the user when the user is experiencing an abnormal medical condition.

Figure 6:
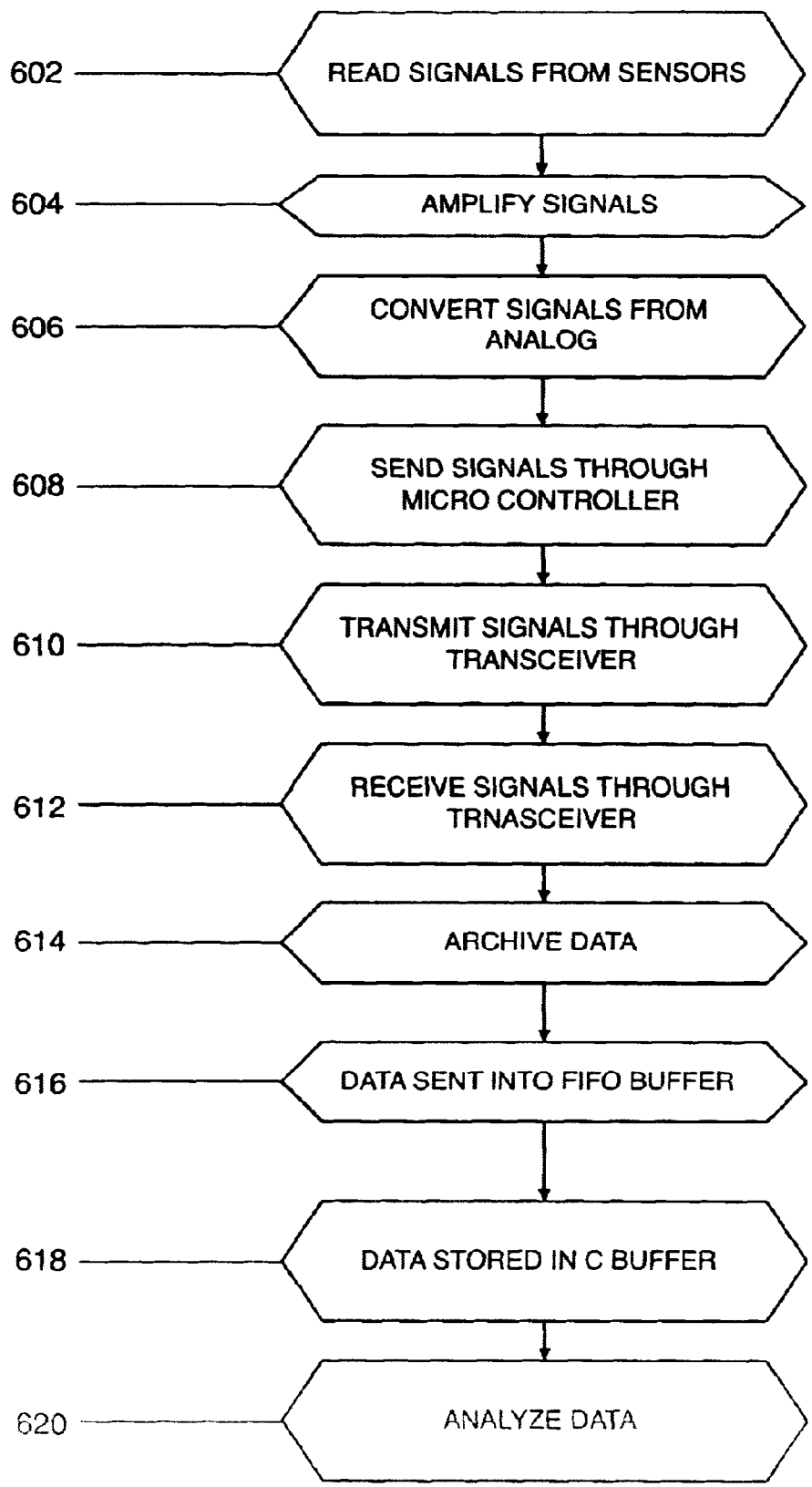
FIG. 6 is a flowchart of a process for receiving and sending information from the portable information device to the information-processing device.

FIG. 6 is a flow chart of a process for receiving and sending information from portable information device 100 to the information-processing device 200. In this process, in step 602, signals are read from sensors 120. These signals, in the case of ECG signals, which measure electrical impulses from the heart, are the pulse rate and the heartbeat of the user. Other signals relating to the health and environment of the user may also be combined. Next, in step 604, these signals are then amplified by amplifier 130. In step 606, these signals are then converted from analog to digital using analog to digital converter 140. This conversion of the signals reduces the bandwidth necessary for transmitting the signals.

In step 608, these signals are sent through a MICRO controller, which turns this information into a series of 8 bit ECG bytes, wherein N bytes of information are combined into one packet, which is sent to transceiver 160. Next, in step 610 this information is sent through transceiver 160, whereby it is then received in step 612 in to transceiver 210 in information processing device 200. Next, in step 614, this information is archived.

In step 616, this information is then stored into FIFO buffer 214. This information is then smoothly read out so that the discrete packets of information can now be read out as a continuous flow of information. Next, in step 618, the current value is read into C buffer 216, which always contains the latest ECG fragment of a given length. In step 620, this information is then sent for analyzation by feeding this information from C-Buffer 216 to information analyzer 230.

Figure 7A:
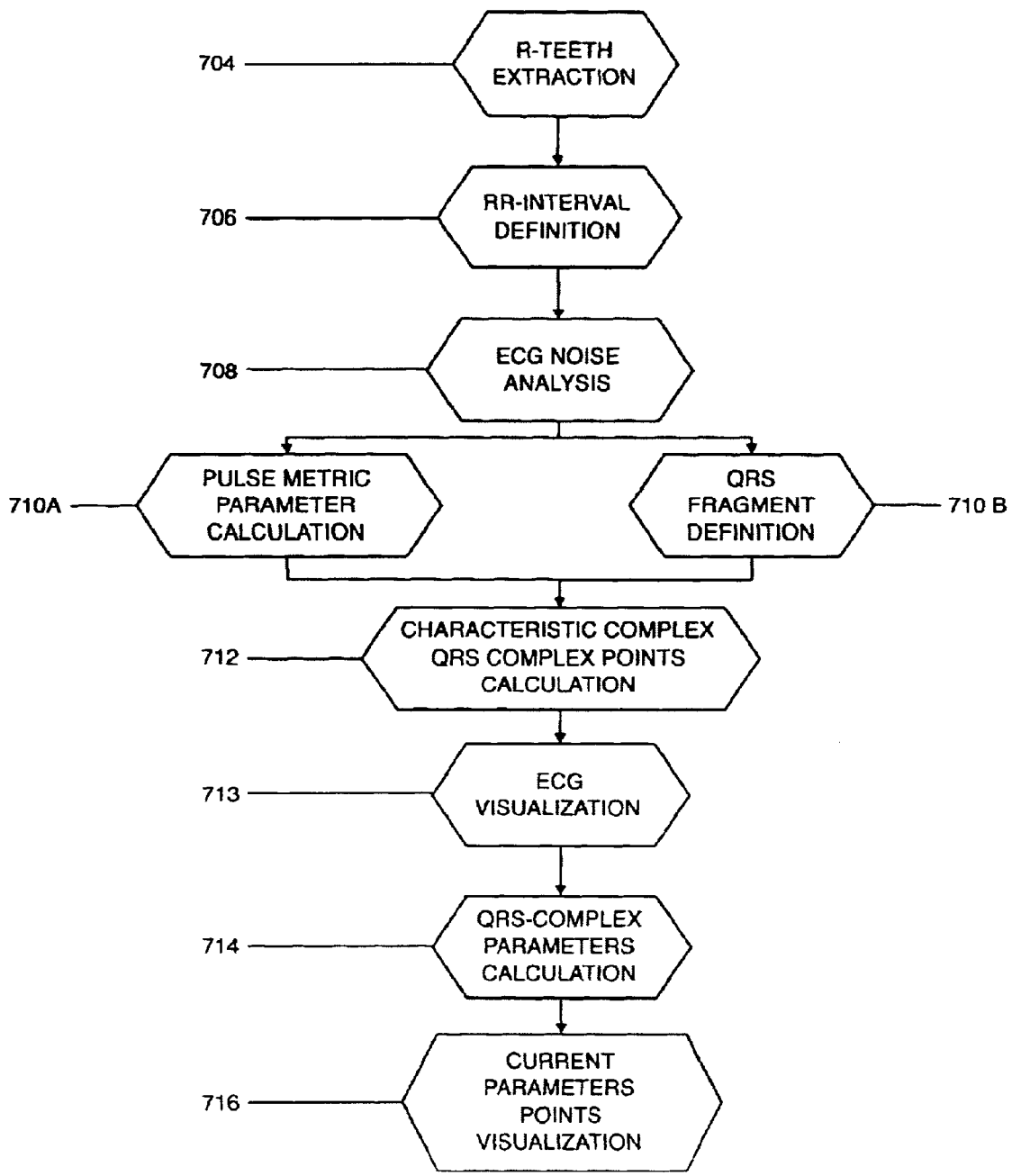
FIG. 7A is a flow chart of a process for extracting and calculating a plurality of parameters from the information sent from the portable information device.

FIG. 7A is a flow chart of a process for extracting and calculating from an ECG reading a plurality of points contained in a QRS wave and then plotting this wave. In addition, this process includes the calculation of parameters from the information contained in these points. These parameters are known in the art and are used to aid a health care professional in the evaluation of a patient or user of cardiac equipment. These parameters are: 1) pulse rate; 2) immediate alteration of pulse rate; 3) R—R interval; 4) premature beats; 5) Group of premature beats; 6) The atrial fibrillation-flutter; 7) ST-segment depression/elevation; 8) T-wave inversion; 9) Width of Q-wave; 10) Ratio of Amplitude Q-wave to amplitude R-wave; 11) Amplitude of R-wave; 12) Width of QT-interval; 13) Width of QRS complex; 14) Width of PQ-interval; and 15) Standard deviation of the average normal-to-normal R—R-intervals.

For example, in step 704, the information in information analyzer 230 is manipulated so that a series of R-peak are extracted. R-peaks are points on the ECG wave or QRS fragment shown in FIG. 8A and in FIGS. 9A, 9B, and 9C, whereby these peaks are the periodic maxima of this wave. To find the R-peaks, the information analyzer determines the highest increment of amplitude A in the wave across a particular period D (FIG. 9A–9C).

This determination is essentially made through the following formulas:

$$(V-V_1) > A_1 \quad (1)$$

OR $$(V-V_2) > A_2 \quad (2)$$

Whereby

V—is the amplitude at a current point along the QRS fragment;

$V_1$ is the amplitude in point $(t-d_1)$;

$V_2$ is the amplitude in point $(t-d_2)$;

t is the current time;

$d_1$, $d_2$, $A_1$ and $A_2$ are empiric constants whereby as an example:

$d_1 = 75$ ms $A_1 = 5$ mv $d_2 = 40$ ms $A_2 = 3$ mv

Thus, a point along the ECG wave is determined as a R-peak, if the amplitude increment exceeds amplitude $A_1$ for period $D_1$ or amplitude $A_2$ for period $D_2$. Formula (1) reflects a clearly is defined peak, while formula (2) reflects a weakly defined peak with small amplitude. After an approximate R-peak is identified the point undergoes refinement within time period $d_p$ (FIG. 9B) Empiric values of $d_p$ and $A_d$ are 200 ms and 1 mv correspondently.

Once these R-peaks have been determined, in step 706 information analyzer 230 defines an R—R interval. The R—R interval is defined as the distance between two consecutive R-peaks. Once the R—R intervals have been determined, then in step 708, information analyzer 230 can determine the amount of noise in the reading of the ECG signal. The noise level analysis is performed within the current R—R interval shown in FIG. 8B. If this noise level exceeds predefined limit current R—R interval is disregarded. This noise level analysis is essential because it excludes from further analysis R—R intervals with artifacts exceeding acceptable level. The noise in ECGs is generated primarily by skeletal muscle activity. Other sources of noise include physical contact with any of sensors 120 and 122, or a loose-connection between the user's body and sensors 120 and 122, interference from outside sources such as cellular telephones, microwaves from microwave ovens, television sets, alarm clocks, or electromotive forces or EMF from electrical appliances, which was not filtered by the Amplifier.

If the noise exceeds acceptable level, R—R interval is excluded from further calculations. A visual indication of the relative noise level may be presented to the user. Noise level analysis is performed within current R—R interval using formulas as followed:

Starting with N=0, then:

for each given point j from interval $[R_{i-2}+e_1, R_i-e_1]$:

if $|(V_j-V_{j-1})| > 2^m$ and $|(V_j-V_{j+1})| > 2^m$, then $N=N+2^m$, $m=3 \ldots 0$, $j \in [R_{i-2}+e_1, R_i-e_1]$ for each given point j from interval $[R_{i-2}+e_2, R_i-e_2]$ if $(V_j-V_{j-1}) > m$ and $(V_j-V_{j+1}) > m$, then $N=N+m$, $m=30, 20$, $j \in [R_{i-2}+e_2, R_i-e_2]$:

where:

$e_1$, $e_2$—indentations from threshold points (threshold point are empiric values equal 75 ms and 115 ms correspondently);

$V_j$—amplitude in point j;

N—noise level value.

Once the significant R—R intervals have been selected, the data is sent to information analyzer for a pulse metric parameter calculation in step 710A and a QRS fragment definition in step 710B. Essentially, steps 710A and 710B determine the plurality parameters discussed above.

For example, the calculation of the Pulsometry parameters include the calculation of the pulse rate, premature beats, and atrial fibrillation flutter. The pulse rate is based upon R—R intervals whereby the pulse rate is calculated as the average value of an R—R interval of the last 4 R—R intervals:

$$P_N = \frac{60 \cdot 1000 \cdot 4}{\sum_i RRi}, i = N - 3, \ldots, N$$

The immediate alteration of the pulse is calculated as:

$$P_a = P_N - P_{N-3}$$

Information analyzer 230 can also determine whether the beats that make up the pulse rate are premature. Premature beats are determined by the following formula:

$$\frac{RR}{RRn} \geq 0.7$$

Wherein:

R—R—the current R—R interval;

R—$R_n$—the "normal" R—R interval;

The "normal" interval is calculated as the average value of the last 10 R—R intervals. The R—R interval is included in the sum if it is not premature or compensated. In this case, the quantity of the extrasystoles is analyzed for a 10 second period. With this design the R—R intervals are updated using the FIFO buffer.

Information analyzer 230 also determines the Atrial fibrillation-flutter, which is calculated as:

$$F = (F1 + F2)/X(\%)$$

wherein

F1—is the extrasystole component

F2—is a variability component

X—is a dynamically calculated value and is typically approximately equal to thirty.

An extrasystole is essentially a premature contraction of the heart, which results in a momentary cardiac arrhythmia. Component F1 is determined by the following formula:

$$F1 = (E/G) * 100,$$

wherein

E is the number of extrasystoles within G number of previous R—R intervals;

G is the number of R—R intervals, which are used for the calculation of the F parameter.

If F1>50%, then F1 is considered equal 50%. The variability of two consecutive R—R intervals is calculated as:

$$F_{RR} = (RR_{max} - RR_{min})/RR_{max} * 100$$

If m1>2 then

F2=S1/m1 wherein,

S1 is the sum of all of the variabilities of the G intervals; or

If m2>2 then

S2 is the sum of all of the variabilities of all G intervals.

If m1≦2 AND m2≦2 then F2=0.

In this case, m1 is the number of R—R intervals (from G intervals), which have a variability of 10% <$F_{RR}$<30%. In addition, m2 is the number of R—R intervals (from G intervals, which have variability $F_{RR}$<10%.

Figure 8A:
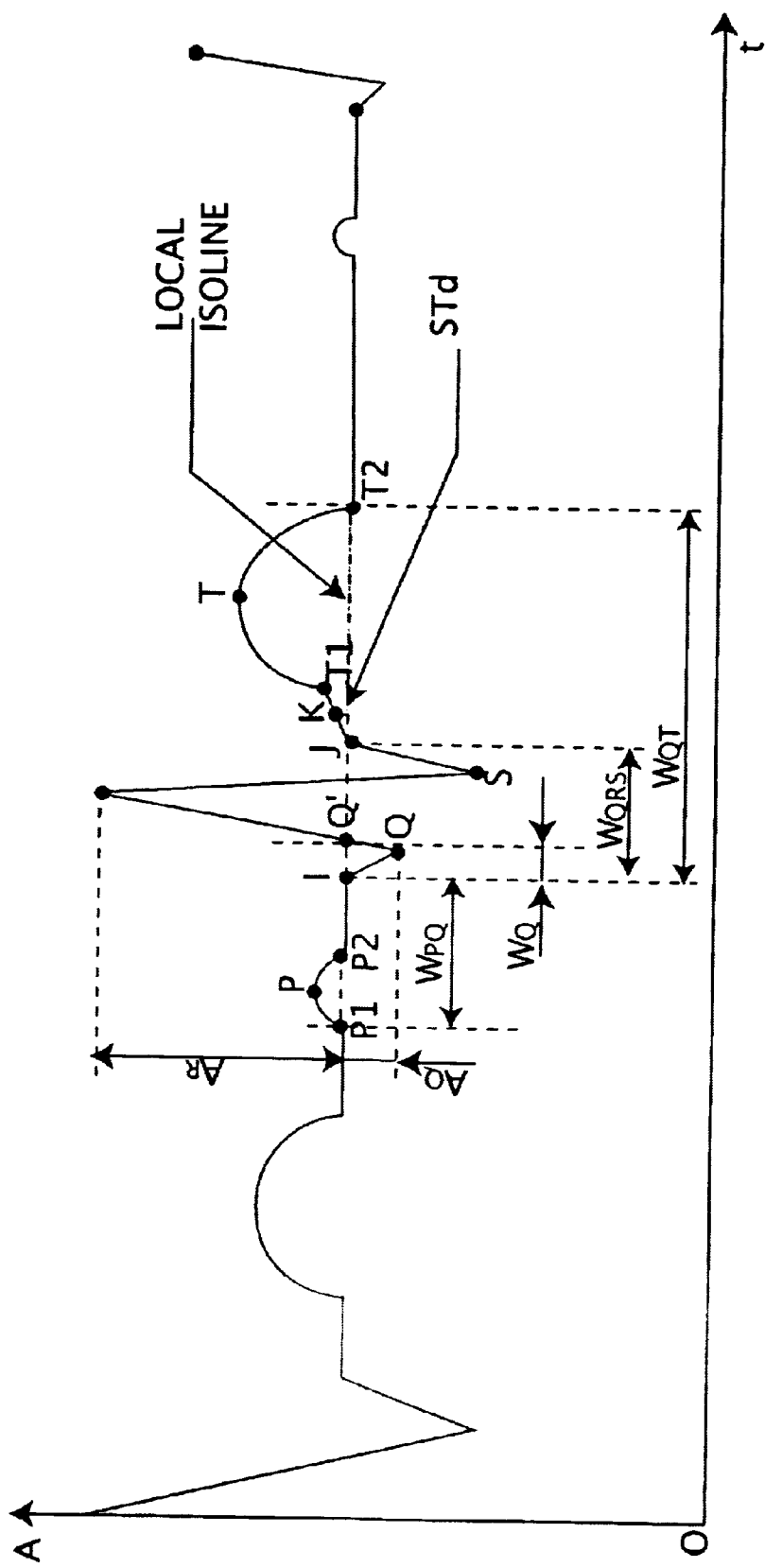
FIG. 8A is a graph relating to the plurality of characteristic points and parameters taken from information obtained from the portable information device.
Figure 8B:
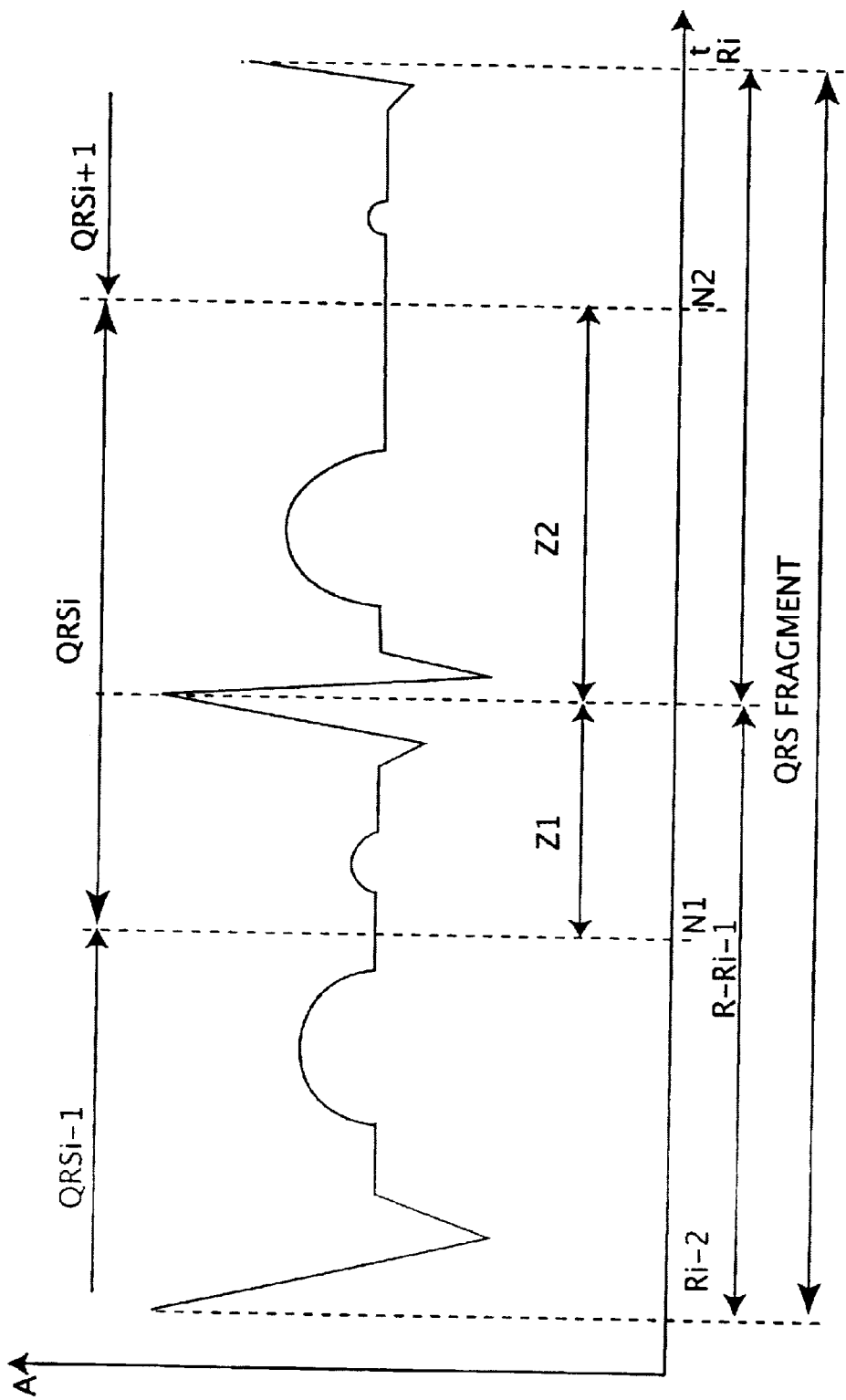
FIG. 8B is a graph showing a division of QRS fragment.

QRS fragment is defined as ECG interval between peaks $R_{i-2}$ and $R_i$ (FIG. 8B).

$QRS_i$ complex (FIG. 8B) is interval [$N_1, N_2$] where $$N_1 = R_{i-1} - Z_1$$

$$N_2 = R_{i-1} + Z_2$$

Initial empiric values of $Z_1$ and $Z_2$ are 40% and 60% correspondently. Points $N_1$ and $N_2$ are refined within further calculations of characteristic points.

Figure 7B:
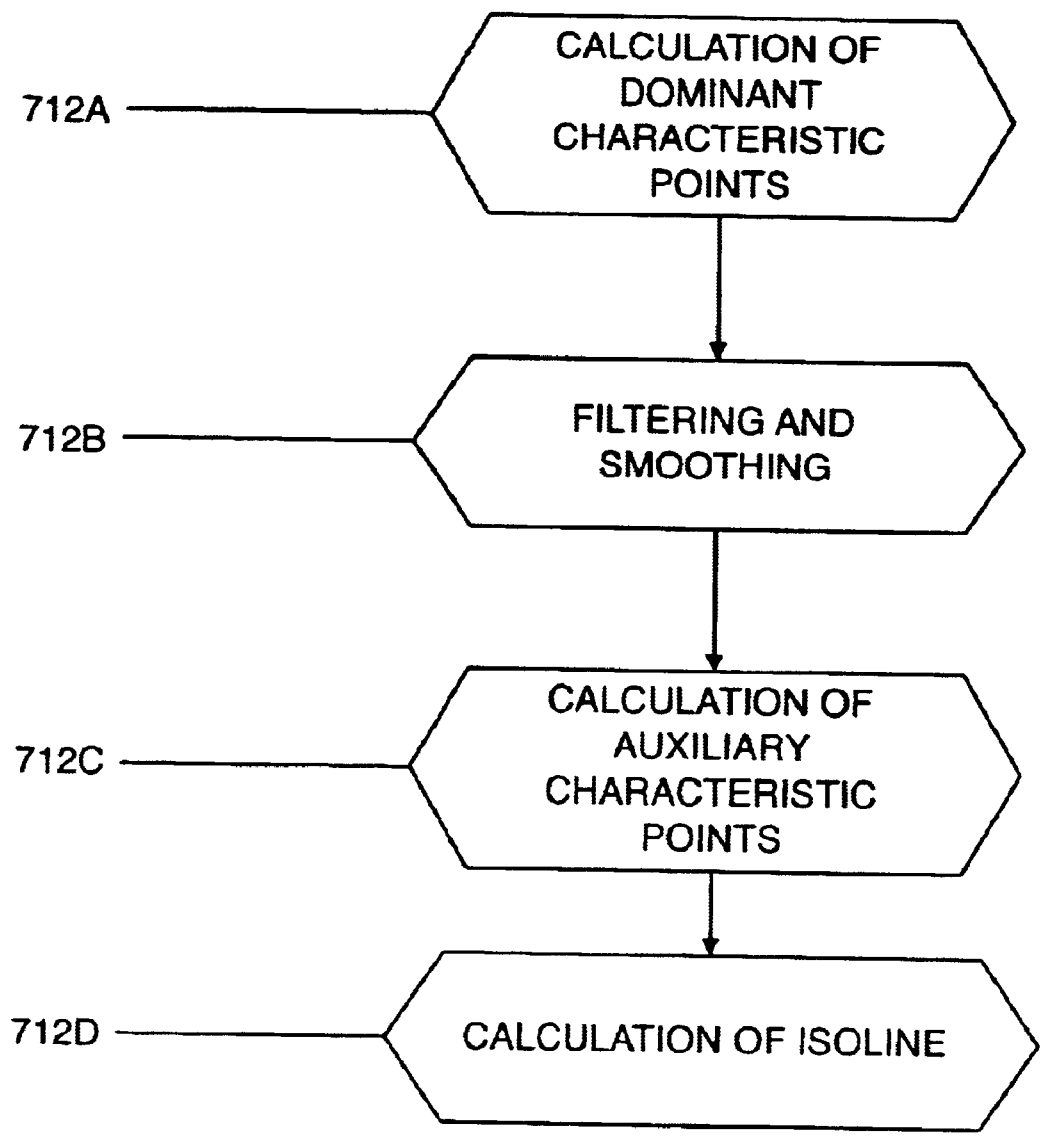
FIG. 7B is a flow chart of a process for determining a series of points along a QRS complex graph shown in FIG. 8A.

FIG. 7B shows the process of step 712, which includes the steps of determining a series of characteristic points of the QRS complex shown in FIG. 8A. In this case, points Q, R, S, J, and P, are known basic or (dominant) characteristic points of the QRS complex shown in FIG. 8A. Points P, I, K, P1, P2, T1, and T2 are defined as auxiliary characteristic points. These points are determined or calculated in a manner similar to point R by a waveform analyzer, which is incorporated into information analyzer 230. Thus, in step 712A, information analyzer 230 calculates points R, Q, S, J, K, I and $I_N$.

Point Q is calculated from the graph in FIGS. 10A–10C in the following manner:

By following the graph from point R to point R–$D_Q$ wherein $$A_{i-1} > A_1 \text{ and } (A_R - A_i) > A_{RQ}$$

Where

A—is the amplitude;

$A_{RQ}$ is an empiric value that can equal 2 mv;

$D_Q$ is an empiric value equal to 75 ms;

Q is a wave shown in FIG. 10A.

By following the graph from point R to point R–$D_Q$ wherein $$(A_i - A_{i-3}) < A_d \text{ and } (A_R - A_i) > A_{RQ}, i = R, \ldots R - D_G$$

Where

A—amplitude and empiric values $A_d$=0.5 mv $A_{RQ}$=2 mv $D_Q$=75 ms;

Q-wave is shown in FIG. 10B.

Approaching point Q from the left and traveling along the graph from point R to point R–$D_Q$ wherein:

$$(d1/d2) \geq Qr \text{ and } (A_r - A_i) > A_{RQ}$$

$$d1 = A_r - A_{i-3}$$

$$d2 = A_{i+3} - A_i$$

Qr=0.45

$A_{RQ}$=2 mv $D_Q$=75 ms

Q-wave is shown in FIG. 10C.

Point S is determined by using probability methods whereby traveling along the graph from point R to point R+$D_s$ and approaching point S the point is identified if:

$$A_{i+1} > A_i \text{ and } (A_R - A_i) > A_{RS} \text{ wherein } i = R, \ldots R+D_S$$

Where

A—is the amplitude;

$A_{RS}$ is an empiric value that can equal 2 mv;

$D_s$ is an empiric value equal to 75 ms;

S is a waveform shown in FIG. 11A.

By following the graph from point R to point R+$D_s$ and approaching point S from the left point S is calculated by a probability formula wherein $$(A_i - A_{i-3}) < A_d \text{ and } (A_R - A_i) > A_{RQ}, i=R, \ldots R-D_s$$

Where

A—amplitude and empiric values $A_d$=0.5 mv $A_{RS}$=2 mv $D_S$=75 ms;

S is a waveform shown in FIG. 11B.

Approaching point S from the left and traveling along the graph from point R to point R–$D_Q$. The point has been identified if:

$$(d1/d2) \geq Sr \text{ and } (A_r - A_i) > A_{RS}$$

where $d1 = A_i - A_{i-3}$ $d2 = A_{i+3} - A_i$

Sr=0.3

$A_{RS}$=2 mv

S is a waveform shown in FIG. 11C.

After identification, points Q and S are refined if they are not defined clearly.

Approaching point J from point S to point S+$D_J$ The point has been identified if $$(A_{i-3} - A_i) < A_d \, i=S, \ldots, S+D_j,$$

where

A—amplitude;

$A_d$=0.5 mv;

$D_j$=75 ms;

If point J has not been identified it is considered equal to point S.

Approaching point I from point Q to point Q–$D_I$. The point has been identified if $$(A_{i-3} - A_i) < A_d \, i=Q, \ldots, Q-D_I$$

where

A—amplitude;

$A_d$=0.5 mv $D_I$=40 ms

If point I has not been identified, it is considered equal to point Q.

Point K has been defined as (J+$D_j$, $A_{j+Dj}$)

where:

$D_j$=80 ms;

$A_{j+Dj}$ is amplitude in point J+$D_j$

Next, in step 712B, after point Q, R, S, I, J, K have been identified, information analyzer 230 filters and smoothes QRS fragment using Cubic Spline Interpolation method and sends for visualization as shown in FIG. 7A, step 713.

In step 712C, points T, T1, T2, P, P1, P2 are calculated.

Point T is identified using one of probability methods staring from the most reliable. Point T is defined by three geometrical methods depending on the form of point T.

First, from point J to point N2, the point has been identified if the distance from point (i, $A_i$) to line (I, $I_N$)>$T_{Amin}$, where:

(i, $A_i$)—maximum point $T_{Amin}$=2 mv

This method is used for identification of "normal" point T. T waveform is shown in FIG. 12A.

If "normal" point T is not found, inverse point T is identified.

(i, Ai)—is a minimum point;

TAmin=8

T-wave form is shown in FIG. 12B.

Approaching from point J to point N2 point T has been identified if:

$$(A_i - A_{i+5}) > A_d, i=J, \ldots N2,$$

where

A—amplitude $A_d$=5 mv

T-wave from is shown on FIG. 12C.

The system proceeds through these steps whereby the system first tries to find the T wave using the point shown in FIG. 12A; next if the system is not able to find the T wave it applies a second algorithm whereby it looks to find it based upon the point shown in FIG. 12B.

If the point is still not identified, the system concludes that point T doesn't have clearly defined maximum whereby the third algorithm is applied as shown in FIG. 12C.

Point T2 (the end of the T-wave)

Approaching T from N2, point T2 has been identified if: $A_i > A_{i+1}$; or if the angle contained by the X axis and the current point becomes less than the previous angle contained, and this tendency continues within a 40 ms time period.

The similar method is used to calculate point T2 if T-wave has an inverse shape.

Point T1 (beginning of T-wave)—the similar calculation of T2 point methods are used.

Point P has been identified by approaching from point I to N1 wherein point P has been identified if:

$$A_i - A_{i-5} > A_d \text{ and } A_i - A_{i+5} > A_d;$$

where $A_d$=2

Point P2 is identified using algorithms similar to the algorithms applied to the identification of point T2.

Point P1, which is the beginning of the P wave is defined using the formula:

$$P1 = P - (P2 - P)$$

Point $I_N$ (point I for the next QRS-complex) is identified as point I of QRS-complex.

Next, in step 712D, the local isoline is calculated. The local isoline is considered a straight line between points L1 and L2. This isoline is usually bounded by point P1 on the first left point or point I, and the right most point can be either point T2 if that point exists, otherwise that point is $I_N$. If the angle of the local isoline exceeds 35° then the isoline is considered invalid.

In step 714, after defining all of the characteristic points of the QRS-complex, the QRS complex parameters are calculated. These QRS complex parameters include the ST-segment depression/elevation ($ST_d$); the width of the Q-wave ($W_Q$); amplitude of Q-wave; the width of the QRS complex ($W_{QRS}$); the width of the PQ interval ($W_{PQ}$); the width of the QT interval ($W_{QT}$); the amplitude of the R wave ($A_R$); the T wave inversion, which is the position of the T wave over the local isoline; and the ratio of the amplitude of the Q-wave ($A_Q$) to the amplitude of the R wave ($A_R$)

These elements are calculated through the following formulas: The ST-segment depression elevation or ($ST_d$) is defined as the distance from point k to the isoline.

The increase of the Q wave is calculated as:

$$W_Q=((I-Q)*1000)/F(ms)$$

Wherein F is the frequency of the ECG digitization.

The increase of the Q wave amplitude is defined as Q/R or $$A_{QR}=((A_I-A_Q)/(A_R-A_I))*100\%$$

wherein $A_I$ is the amplitude at point I;

$A_Q$ is the amplitude at point Q; and $A_R$ is the amplitude at point R.

The sudden increase of the QRS duration is calculated as $$W_{QRS}=((J-I)*1000)/F(ms)$$

wherein

F=is the frequency of ECG digitization.

In this case the increase of the PQ interval is calculated as:

$$W_{PQ}=((I-P_2-2*P)*1000)/F(ms)$$

wherein

F=is the frequency of ECG digitization.

The increase of the QT interval is calculated as:

$$W_{QT}=((T_2-I)*1000)/F(ms)$$

wherein

F=is the frequency of the ECG digitization.

The decrease of the R wave amplitude is calculated as:

$$A_{RD}=(A_R-A_I)*0.2(mv).$$

Finally the T wave inversion has been defined within the identification of point T.

In step 716 these parameters are averaged using a number of significant QRS complexes.

Once all of these points have been calculated, in step 718, these parameters are placed upon the QRS wave so that a user can visualize these points or parameter points.

Figure 13:
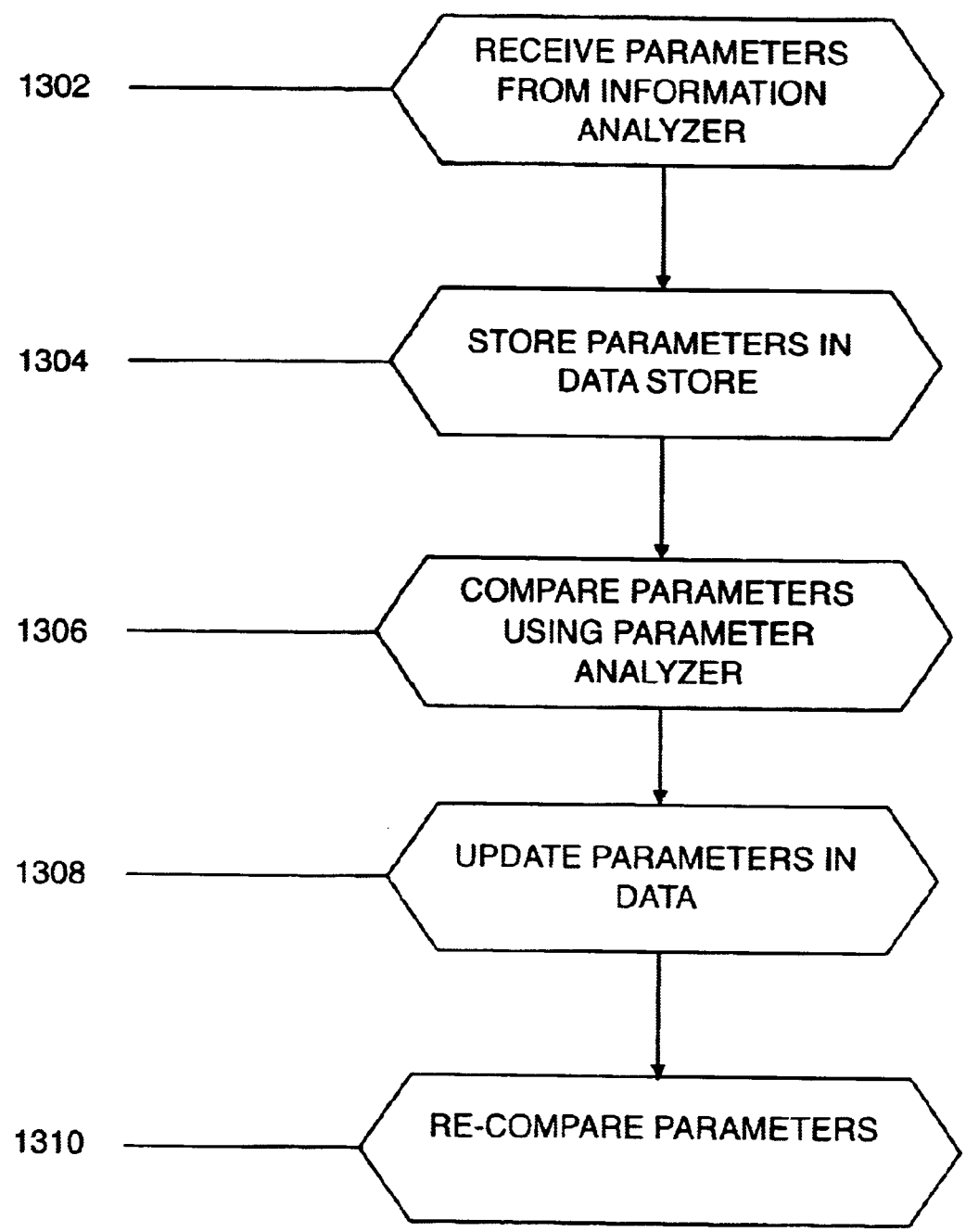
FIG. 13 is a flow chart showing an analysis of the plurality of parameters.

Now that the plurality parameters have been determined from the QRS wave, they are compared in real time with a set of stored parameters in storage device 240. FIG. 13 is a flow chart showing an analysis of the plurality of parameters. This flow chart symbolizes the process that parameter analyzer 250 goes through to determine plurality distinct parameters relating to a person's health. For example, in step 1302, the plurality of parameters are received from information analyzer 230 and in step 1304, these parameters are next stored in storage device 240. Next, in step 1306, parameter analyzer 250 compares the plurality parameters recently received from information analyzer 230 with a set of a plurality of preset parameters stored in a database having a table in information storage device 240 and shown in FIG. 14. These plurality of preset parameters are determined through a series of former users. Essentially, whenever a user experienced an actual medical condition or a medical symptom, these plurality parameters were recorded and used to make an evaluation of a patient. Over time, the preset values for these plurality parameters were determined by the average readings for a series of patients experiencing abnormal medical conditions.

Once the parameters have been compared in step 1306, in step 1308, parameter analyzer 250, a medical professional, or the user, can choose to update the preset values using an average of that user's values, or reset a new range of preset values. These updated preset values can be placed either in data storage device 240 or into personal data storage device 245. In that way, these preset values can be customized for each user. If the preset values are updated, then the original preset values are placed in an inactive file in data store 240 while the new preset values are placed in an active file in data store 240.

In step 1310 the parameters fed from information analyzer 230 are then re-compared to this new set of pre-set values so that abnormality identifier 260 can determine whether a user is experiencing an abnormal medical condition.

Figure 15:
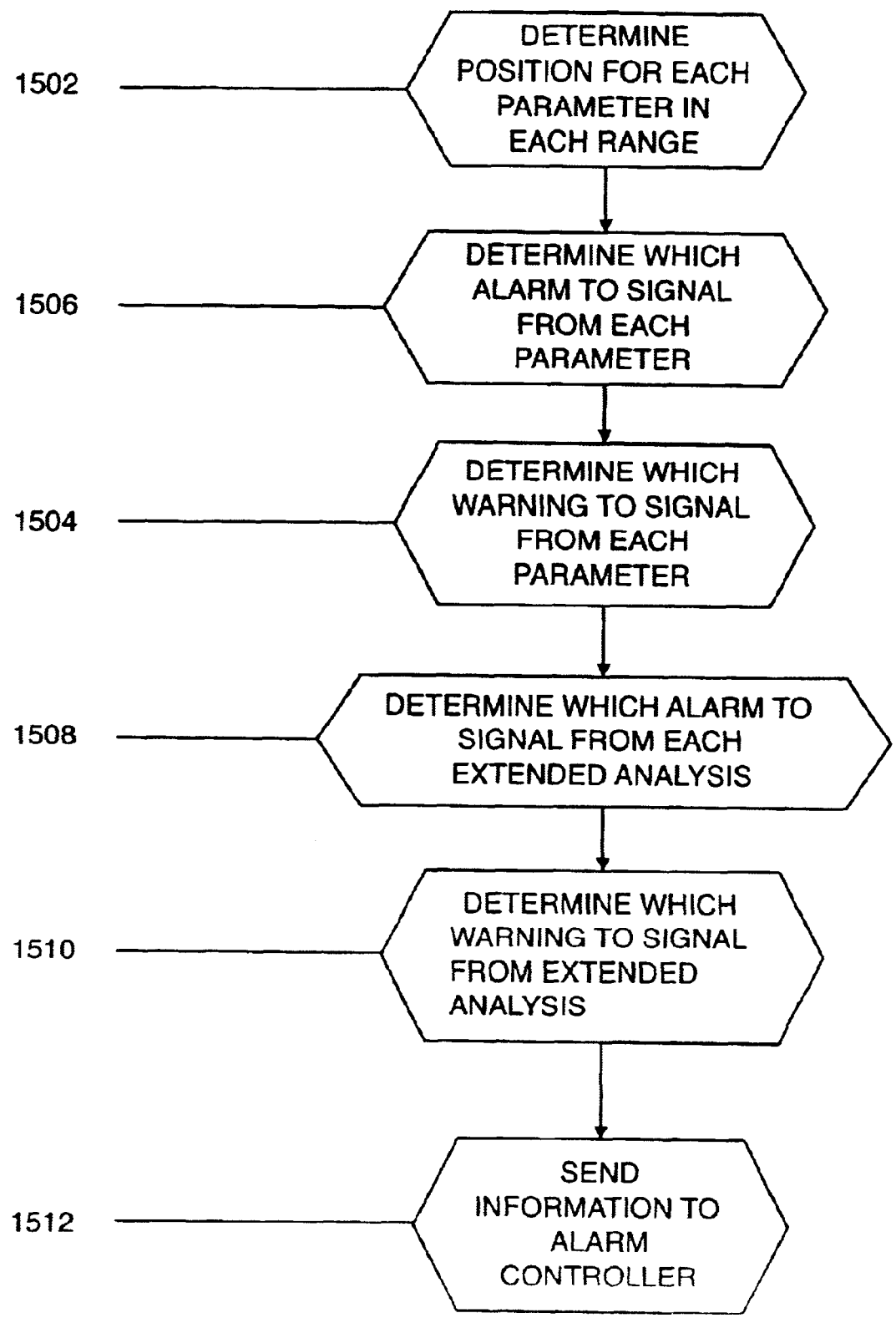
FIG. 15 is a flow chart for predicting an occurrence of a health risk using the table of parameters.

FIG. 15 is a table for determining whether to trigger an alarm depending on the comparison of the present time parameters with the preset parameters stored in data store 240.

Essentially, when a reading of a parameter falls between a low value and a high value, on most or all of the parameters, then the user would be considered in a safe zone. However, when one or more of the parameters has a reading that falls between a low or very low value or a high or very high value, then the user may receive an alarm or just a warning. However, if the parameter value falls below a very low value or above a very high value then the user would definitely receive an alarm. Essentially there are at least twenty-two possible permutations between abnormal readings of the fifteen parameters and the possible abnormal medical condition.

For example, in step 1502, abnormality identifier 260 determines the position for each of the parameter readings, in each range. Next, in step 1506, abnormality identifier 260 determines which alarm to signal from each parameter reading. In step 1504, abnormality identifier determines which warning to signal from each parameter. In addition, there are a series of warnings or alarms that may be triggered as a result of extended analysis which includes assessment of complicity of two or more abnormal parameters, analysis of certain parameters over extended time period, and overall risk assessment based on the patient's medical, history, age, weight, and gender. Therefore, in step 1508, abnormality identifier 208 determines whether an extended analysis will signal an alarm and/or generate an external stimuli. In addition, in step 1510, abnormality identifier 260 determines which warning to signal from the extended analysis. Finally in step 1512 this alarm and warning information is sent on to alarm controller 280 for further processing.

FIGS. 16A–16F shows a series of tables that show the eighteen warnings and alarms and their corresponding threshold parameters. For example, alarm or warning A1 would signal one of the following possible clinical abnormalities: sick sinus node syndrome; slow ventricular rhythm; AV—block II–III degree. Alarms or warnings A2 and A3 would signal a paroxysm of tachycardia. Alarm A4 would signal a sudden heart block or (max syndrome) or an AV block II–III degree. Alarm AS would signal a sinus arrest or a cardiac arrest. Alarm A6 would signal Extrasystoles. Alarm A7 would signal group Extrasystoles. Alarm A8 would signal paroxysm of atrial fibrillation flutter.

Alarms A9 and A10 would signal myocardial ischemia, while alarm All would also signal myocardial ischemia as well as myocardial infarction and bundle branch blocks. Alarms A12 A13 and A14 would signal myocardial infarction, and bundle branch blocks. Alarms A15, and A16 would signal a high risk of ventricular tachyarrhythmias. Alarm A17 would signal bundle branch blocks, while Alarm A18 would signal an AV-block.

Alarms $GE_{A7}$, $ST_{W9}$, $ST_{A9}$, $ST_{W10}$, $ST_{A10}$, $W_G$, and $A_G$ would signal cardiac events and prognoses resultant of extended analysis.

Figure 17:
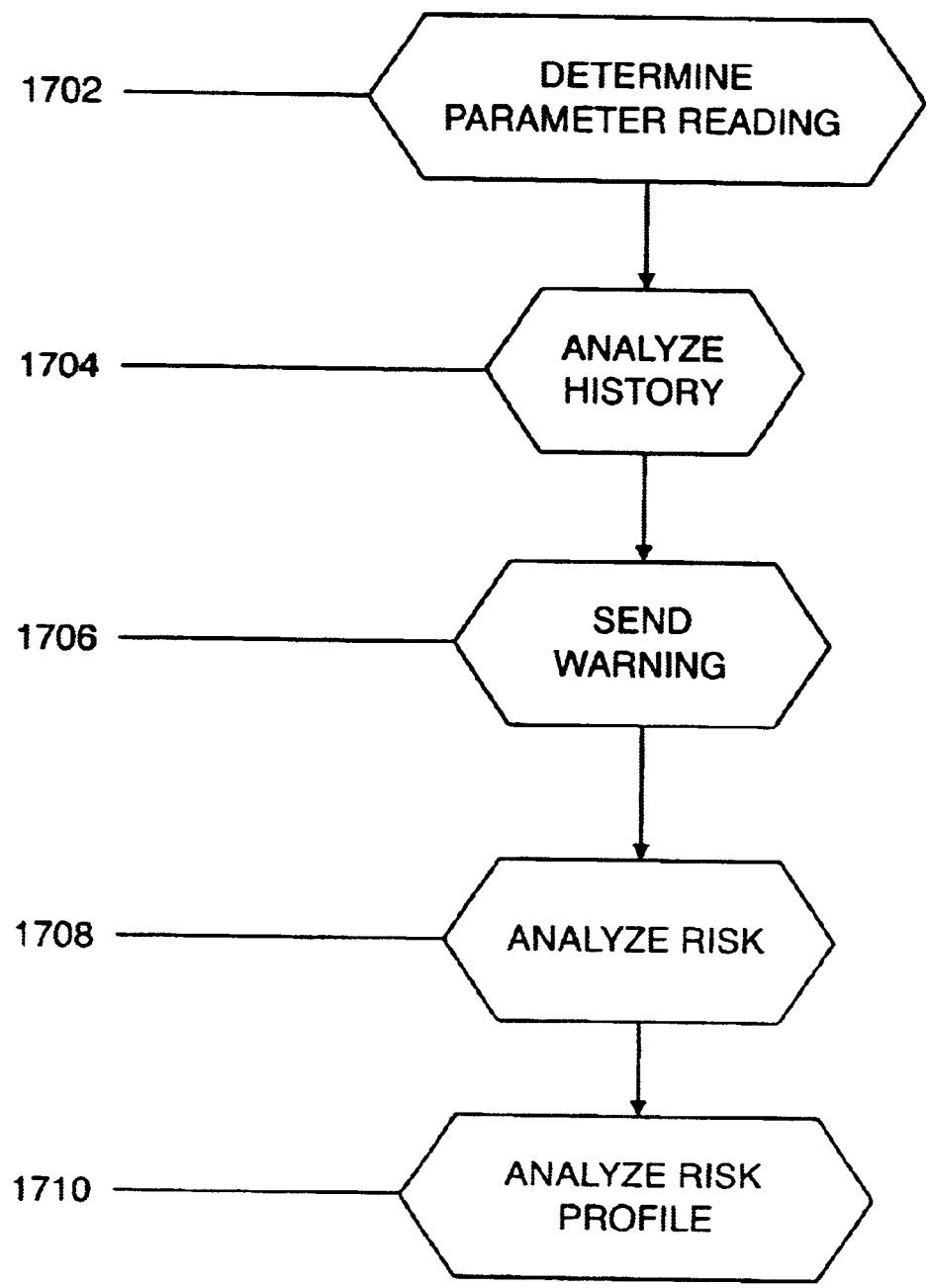
FIG. 17 is a flowchart showing a process for triggering a warning based upon an inference risk analysis.

This model can be used to predict future problems as well. For example, FIG. 17 shows the process for determining whether to send a warning to a user based upon readings from the parameters and the user's medical history. In step 1702, the parameter reading is determined wherein if this reading falls within a warning range, the system proceeds to step 1704 whereby the user's medical history is analyzed. Thus, if the user is overweight with high blood pressure and has had a history of heart attacks, an abnormal parameter reading would increase that user's risk for an abnormal medical condition such as a myocardial infarction.

Thus, in step 1706 the risk of such a condition is analyzed using the history of that user as well as a history of conditions for a number of past users. In this case, the accuracy of this step will continue to improve as the user continues to wear portable information reader 100. The preset values for that user could be continuously updated and compared to a history of values for that user as well as other users that have been tested.

Next, in step 1708 the risk profile of the user is analyzed. The risk profile is based upon empirically derived data and does not require any specific input from the user. The risk profile is essentially a sensitivity setting for the alarm. Thus, if the alarm is set to be highly sensitive, then a warning may sound at the slightest abnormality in parameter readings. Finally, if the criteria have been met, then in step 1710 the alarm is sounding sending a warning to that user.

To determine a warning range for a user, step 1702, which includes the step of determining a parameter reading, which includes determining the RR reading for a user. This determination includes having parameter analyzer 250 use the following formula to determine whether a user is entering a dangerous range:

$$RR = 1 + \sqrt{1.49 * \left|\frac{STmeas - STinit}{STinit.+STthresh.}\right|^2 + \left|\frac{QTmeas.}{QTnorm.} - 1\right|^2 + \left|\frac{N_1 + 34.91 * N_2 + 73.68 * N_3}{HR}\right|^2}$$

Wherein:

RR—is the complex Relative Risk of sudden cardiac death and development of myocardial infarction.

HR is the heart rate per minute (BPM);

ST init.—ST segment level before observation beginning;

ST meas.—ST segment level at the current moment;

ST thresh.—ST segment threshold normal levels;

QT meas.—QT interval duration at the current moment;

QT norm.—QT interval normal duration determined with the Basset Formula:

$$QTnorm = k * \sqrt{60/HR}$$

k is a constant coefficient of 0.4 for males and 0.37 for females;

N1 is the amount of single ventricular extrasystoles per min;

N2 is the amount of coupled ventricular extrasystoles per min;

N3 is the amount of ventricular tachycardia runs (more than two in a row) per min.

Based upon the RR parameter defined above, the value of the sudden cardiac death and myocardial infarction risk assessment is made. Wherein the higher the number reading for RR the higher the likelihood of risk for medical complications.

Essentially, in this step, the remote medical device couples with a computer to perform the associated method to calculate multiple parameters to predict when a patient will experience a medical abnormality listed above.

Figure 18:
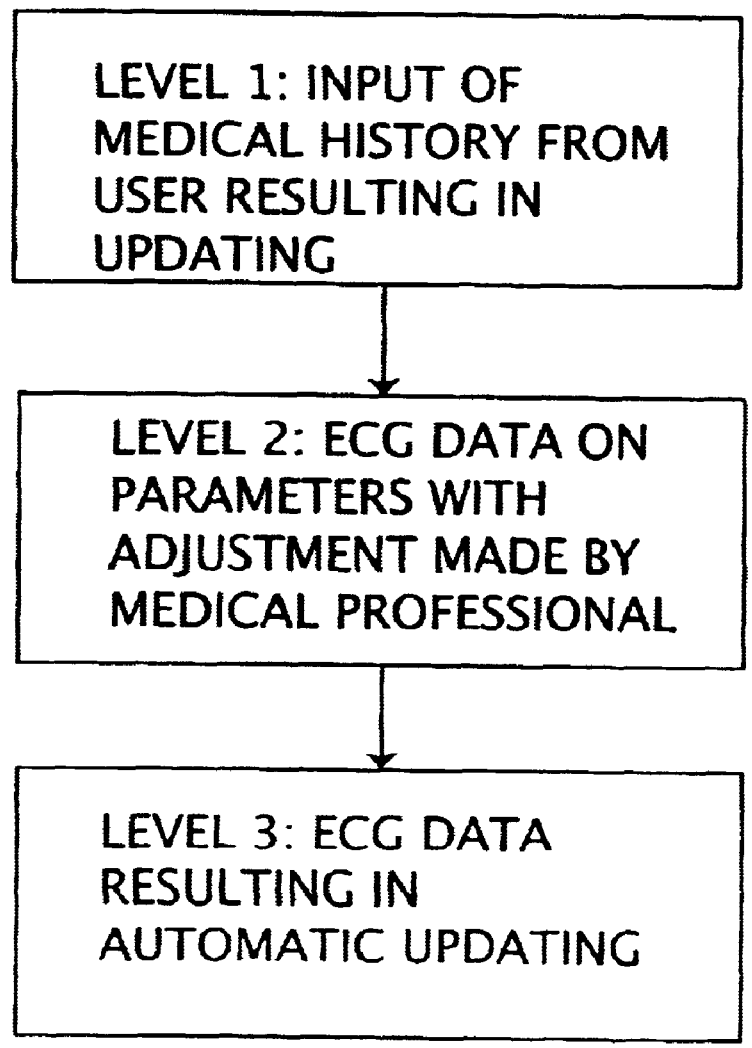
FIG. 18 is a flowchart showing the process of three levels of adaptive changes to parameter threshold conditions.

The system as shown in FIG. 18 uses three level adaptively to adjust the range of threshold parameters. The three levels are:

Level 1: The baseline (normal) threshold levels which are preset in the system which are well known to practitioners will be adjusted considering age, gender, weight, and/or medical history.

Level 2: The system analyzes the log file of cardiac events and patient historical data, which are used to determine new range of parameters. These new parameters should be confirmed by medical personnel and entered into the system manually. One or more of the parameters may be the same as the baseline parameters.

Level 3: The system may update some of the parameters automatically. These changes are limited to pre-selected parameters within selected ranges. If the system recommends a change beyond the specified range then it becomes a level 2 change.

This device and forecasting method was used to test ten patients for sudden cardiac death and myocardial infarction Risk forecasting. These patients are as follows:

Patient No. 1

Male Born 1945 clinical diagnosis: coronary artery disease, stable angina, and frequent ventricular extrasystoles.

Monitoring Observation Data:

ST segment depression (ST meas.): 3 mv

QT interval duration (QT meas.): 600 ms,

The amount of single ventricular extrasystoles (N1) per min 15,

Coupled extrasystoles (N2)—3

Sequential ventricular extrasystoles (N3) consisting of three complexes—1 episode, Heart rate 85 BPM.

RR: 5.5

Wherein RR is the sudden cardiac death and myocardial infarction development complex risk (RR) computed with this applicant forecasting method.

The unfavorable prognosis was proven, in two days the patient suffered from acute coronary syndrome and ventricular fibrillation. The patient was successfully resuscitated and adequate anti-ischemic and anti-arrhythmic therapies were assigned.

Patient No. 2

Male born 1937. Clinical diagnosis: coronary artery disease, stable angina.

Monitoring Observation Data:

ST segment depression (ST meas): 2 mv

QT interval duration (QT meas): 400 ms

Amount of single ventricular extrasystoles ($N_1$) per min: 9

Coupled ventricular extrasystoles ($N_2$): 1

Sequential ventricular extrasystoles ($N_3$): 0

Heart Rate: 72 BPM

RR: 3.5

The unfavorable prognosis was proven, wherein in one month the patient had suffered from development of a complex myocardial infarction.

Patient No. 3

Male born 1947. Clinical diagnosis: Arterial hypertension, frequent ventricular extrasystoles.

Monitoring Observation Data:

ST segment depression (ST meas): 0 mv

QT interval duration (QT meas): 500 ms

Amount of single ventricular extrasystoles ($N_1$) per min: 12

Coupled ventricular extrasystoles ($N_2$): 2

Sequential ventricular extrasystoles ($N_3$): 2

Heart Rate: 78 bpm

RR: 4.0

Unfavorable prognosis was proven, in seven days the patient has suffered from cardiac arrest resulting from ventricular fibrillation. Patient died despite having resuscitation methods performed on him.

Patient No. 4

Male born 1937 clinical diagnosis: coronary artery disease, stable angina.

Monitoring Observation Data:

ST segment depression (ST meas): 1 mv

QT interval duration (QT meas): 400 ms

Amount of single ventricular extrasystoles ($N_1$) per min: 0

Coupled ventricular extrasystoles ($N_2$): 0

Sequential ventricular extrasystoles ($N_3$): 0

Heart Rate: 66 bpm

RR: 2.2

The patient was under observation for 3 months, there were no unfavorable episodes.

Patient No. 5

Male born 1945. Clinical diagnosis: arterial hypertension.

Monitoring Observation Data:

ST segment depression (ST meas): 0 mv

QT interval duration (QT meas): 360 ms

Amount of single ventricular extrasystoles ($N_1$) per min: 0

Coupled ventricular extrasystoles ($N_2$): 0

Sequential ventricular extrasystoles ($N_3$): 0

Heart Rate: 68 bpm

RR: 1.0

The patient was under observation for three months, there were no unfavorable episodes.

Patient No. 6

Male born 1944, clinical diagnosis: coronary artery disease stable angina.

Monitoring Observation Data:

ST segment depression (ST meas): 3 mv

QT interval duration (QT meas): 370 ms

Amount of single ventricular extrasystoles ($N_1$) per min: 0

Coupled ventricular extrasystoles ($N_2$): 0

Sequential ventricular extrasystoles ($N_3$): 0

Heart Rate: 82 bpm

RR: 4.7

An unfavorable prognosis was proven. In 4 days the patient has suffered from the development of acute myocardial infarction complicated by pulmonary edema. The patient was repeatedly hospitalized and died in 7 hours.

Patient No. 7.

Male born 1960. Clinical diagnosis post myocardial sclerosis.

Monitoring Observation Data:

ST segment depression (ST meas): 0 mv

QT interval duration (QT meas): 600 ms

Amount of single ventricular extrasystoles ($N_1$) per min: 0

Coupled ventricular extrasystoles ($N_2$): 0

Sequential ventricular extrasystoles ($N_3$): 0

Heart Rate: 60 bpm

RR: 1.5

The patient was under observation for 2 months, there were no unfavorable episodes.

Patient No. 8

Male born 1960 clinical diagnosis: arterial hypertension.

Monitoring Observation Data:

ST segment depression (ST meas): 0 mv

QT interval duration (QT meas): 400 ms

Amount of single ventricular extrasystoles ($N_1$) per min: 19

Coupled ventricular extrasystoles ($N_2$): 2

Sequential ventricular extrasystoles ($N_3$): 1

Heart Rate: 66 bpm

RR: 3.5

In 45 minutes the patient suffered from developed stable ventricular tachycardia, which was stopped with defibrillation.

Patient No. 9.

Male born 1944. Clinical diagnosis: coronary artery disease, myocardial infarction, and unstable angina.

Monitoring Observation Data:

ST segment depression (ST meas): 3 mv

QT interval duration (QT meas): 550 ms

Amount of single ventricular extrasystoles ($N_1$) per min: 18

Coupled ventricular extrasystoles ($N_2$): 2

Sequential ventricular extrasystoles ($N_3$): 1

Heart Rate: 82 bpm

RR: 5.3

Unfavorable forecast was proven. In one hour the patient has suffered from the development of acute myocardial infarction. The patient was repeatedly hospitalized and died in one hour.

Patient No. 10

Male born 1955. Clinical diagnosis: coronary artery disease, myocardial infarction, and unstable angina.

Monitoring Observation Data:

ST segment depression (ST meas): 3 mv

QT interval duration (QT meas): 580 ms

Amount of single ventricular extrasystoles ($N_1$) per min: 14

Coupled ventricular extrasystoles ($N_2$): 2

Sequential ventricular extrasystoles ($N_3$): 2

Heart Rate: 80 bpm

RR: 5.8

An unfavorable forecast was proven, in 8 hours the patient has suffered from the development of ventricular fibrillation.

The patient was repeatedly hospitalized and successfully defibrillated.

Essentially this formula for determining RR as stated above can be continually modified so that it becomes more accurate in general and more accurate for each user. Essentially as more patients are analyzed the formula will read as:

$$RR = 1 + \sqrt{K_1 * \left|\frac{STmeas - STinit}{STinit. + STthresh.}\right|^2 + \left|\frac{QTmeas.}{QTnorm.} - 1\right|^2 + \left|\frac{N_1 + K_2 * N_2 + K_3 * N_3}{HR}\right|^2}$$

Wherein the variables are the same as above except:

$K_1$ is a first constant, which was originally 1.49;

$K_2$ is a second constant, which was originally 34.91;

$K_3$ is a third constant, which was originally 73.66.

Constants $K_1$, $K_2$ and $K_3$ can be varied depending upon the clinical data obtained. As more experiments and trials are performed, the constants may be modified to provide more accurate forecasting.

Figure 19:
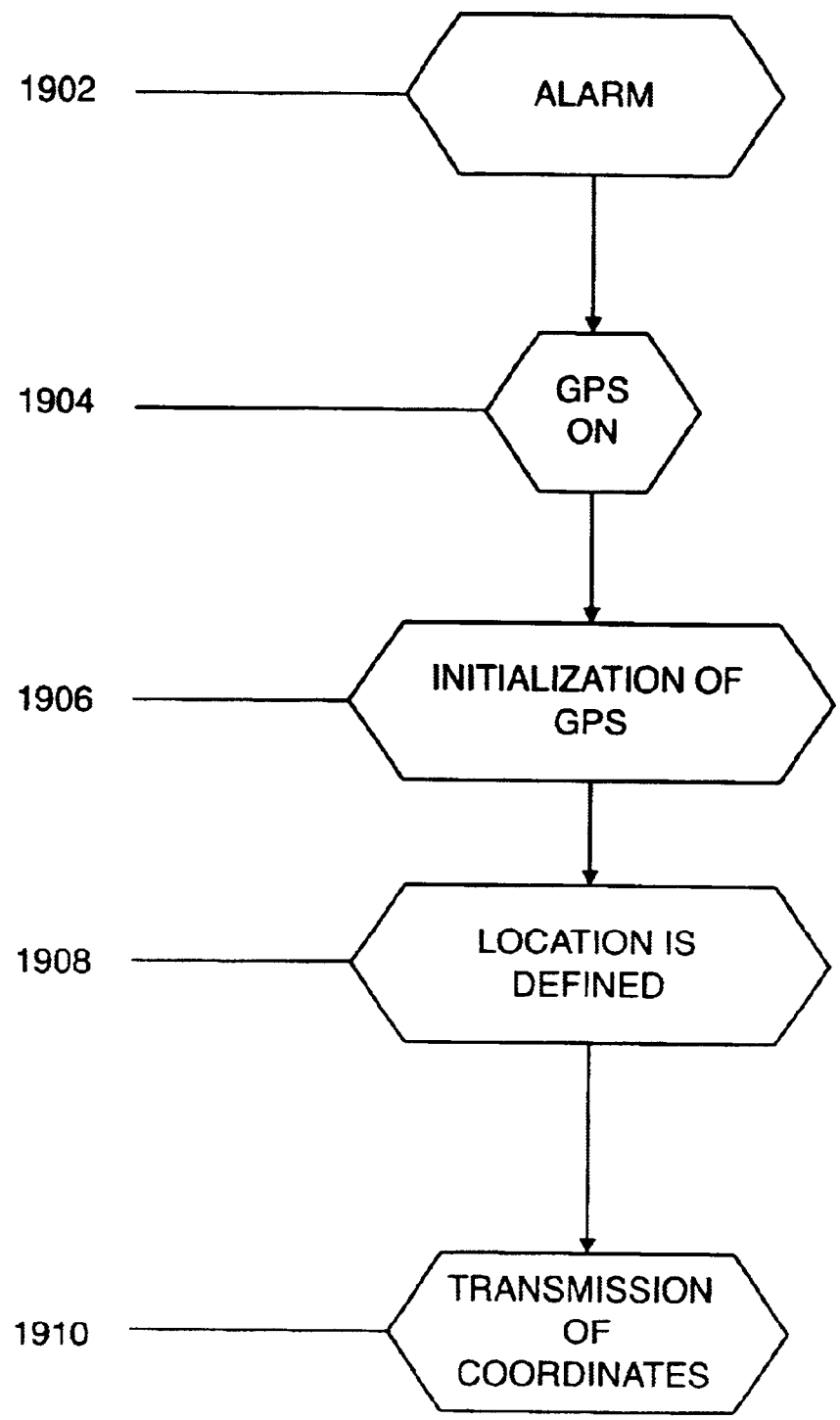
FIG. 19 is a flowchart showing the process for locating a user once the alarm has been triggered.

Once a user starts to have problems, the system can then locate the user so that health care professionals can contact that user. FIG. 19 is a flowchart showing the process for locating a user once the alarm has been triggered. In step 1902 the alarm sends a signal to the GPS unit. In step 1904 the GPS unit turns on and then initializes by sending a signal of the coordinates of the user to remote storage and processing device 300 to locate the user in step 1906. If the GPS system is coupled to remote device 100 then the signal is first relayed to information processing device 200. In step 1908 the user's location is defined. Next, the coordinates of that user are transmitted to central station 300 so that a medical professional can contact a user in person.

Thus, when the user wants to monitor his or her vital signs, that user places a belt containing sensors 120 and 122 on its body. Sensors 120 and 122 read information from that user including information about the user's pulse and heart rate. This information is then sent onto amplifier 130 whereby the signal is amplified before it is fed through an analog to digital (A/D) converter 140. Analog to digital converter 140 sends this information onto MICRO controller 150. MICRO controller 150 transforms this information into blocks of information for transmission by transceiver 160. Transceiver 160 sends this information onto transceiver 210, which receives this information and sends it onto medical information analyzer 230.

Medical information analyzer 230 works along with data store 240 and parameter analyzer 250 to compare this data with a preset amount of data. Parameter analyzer 250 next sends this information onto abnormality identifier 260, which identifies whether any of the signals are abnormal. Next, alarm controller 280 sends this information onto the user as well as a base station housing information storage device 300 through transceiver 284.

One of the major advantages of this invention is that this design monitors the user in a continuous real time fashion allowing a completely free movement of the user.

In addition, another advantage of this invention is that through a series of preset values for a set of plurality parameters, the system can determine whether a user has entered or will enter into an abnormal medical condition such as a heart attack. This set of pre-set values can be continuously updated so that it becomes increasingly more accurate for each user.

Still another advantage of the system is that the system utilized the three level process for determining whether a user will have a future occurrence of an abnormal medical condition. These three levels are:

Instantaneous detection of developing cardiac events;

Evaluation of the complicity of number of minor cardiac abnormalities leading to development of significant cardiac events;

Risk assessment of development Myocardial Infarction and Sudden Cardiac Death.

Accordingly, while several embodiments of the present invention have been shown and described, it is to be understood that many changes and modifications may be made thereunto without departing from the spirit and scope of the invention as defined in the appended claims.

What is claimed is:

1. A process for analyzing a medical condition of a user comprising the following steps:

a) reading at least one signal from the user;

b) transforming said at least one signal into at least one digital signal;

c) extracting a plurality of parameters from said at least one digital signal, wherein said step of extracting a plurality of parameters comprises the following steps:

extracting at least two consecutive R-peaks from said digital signal;

analyzing noise in said digital signal between said at least two consecutive R-peaks found from said step of extracting R-peaks;

determining at least one significant R—R interval;

determining a plurality of pulse metric parameters; and determining a plurality of characteristic points of a QRS complex;

d) analyzing said plurality of parameters and comparing said plurality of parameters to a range in a set of a plurality of preset parameters;

e) determining whether a user has an abnormal medical condition by determining whether said plurality of parameters fall outside of said range in said plurality of parameters; and f) determining whether to trigger an alarm warning the user of his or her medical condition when said at least one of said plurality of parameters fall outside of said preset ranges for said preset parameters.

2. The process as in claim 1, further comprising the step of selecting a particular alarm from a set of a plurality of alarms for the user based upon which of said plurality of parameters fall outside of said range of said plurality of said preset parameters.

3. The process as in claim 1, wherein said step of extracting a plurality of parameters includes extracting a plurality of data points from said at least one digital signal and forming at least one QRS wave from said plurality of data points.

4. The process as in claim 1, wherein said step of determining whether a user has an abnormal medical condition includes the step of setting said range in said plurality of preset parameters based upon an average formed from a plurality of previous users.

5. The process as in claim 1, wherein said step of determining a plurality of pulse metric parameters includes determining:
   a pulse rate;
   a plurality of premature beats; and
   an atrial fibrillation/flutter.

6. The process as in claim 5, wherein said step of extracting at least two consecutive R-peaks from said digital signal includes using the following formula:

$$(V-V1) > A1$$

or $$(V-V2) > A2$$

wherein V is the amplitude at a current point along the QRS fragment;
V1 is the amplitude at (t−d1)
V2 is the amplitude at point (t−d2)
wherein t is the current time and d1, d2, A1, and A2 are empiric constants.

7. The process as in claim 5, wherein said step of determining a pulse rate is calculated using a running average value of a plurality of R—R intervals.

8. The process as in claim 7, wherein said step of determining a pulse rate includes using a running average value of four R—R intervals.

9. The process as in claim 5, wherein said step of determining premature beats includes using the following formula:

$$RR/RRn \leq 0.7$$

whereby RR is the current R—R interval; and
RRn is the "normal" R—R interval.

10. The process as in claim 5, wherein said step of determining said atrial fibrillation/flutter includes using the following formula:

$$F = (F1 + F2)/X\%$$

wherein
   F1 is an extrasystole component;
   F2 is a variability component;
   X is a dynamically calculated value.

11. The process as in claim 1, wherein said step of determining a plurality of characteristic points of a QRS complex includes the steps of:
   determining a plurality of dominant characteristic points;
   determining a plurality of auxiliary characteristic points; and
   determining plurality of QRS complex parameters.

12. The process as in claim 11, wherein said step of determining a plurality of dominant characteristic points includes determining points Q, R, S, J, P and T on a QRS complex.

13. The process as in claim 11, wherein said step of determining a plurality of auxiliary characteristic points includes determining points I, K, P1, P2, T1, and T2.

14. The process as in claim 11, wherein said step of determining a plurality of QRS complex parameters includes:
   calculating a ST-segment depression/elevation;
   calculating a width of a Q-wave (WQ);
   calculating an amplitude of the Q-wave;
   calculating a width of QRS complex;
   calculating a width of PQ interval;
   calculating a width of QT interval;
   calculating an amplitude of R wave;
   calculating a T wave inversion; and
   calculating a ratio of amplitude of Q wave to amplitude of R wave.

15. The process as in claim 1, further comprising a step of smoothing ECG waves by use of a cubic spline approximation.

16. The process as in claim 1, wherein said step of determining an R—R interval involves determination of at least 2 consecutive significant R-peaks.

17. The process as in claim 1, wherein said step of analyzing noise involves filtering out bioelectrical signals generated by skeletal muscle activity and excluding R—R intervals with noise level N exceeding predefined level, wherein noise level N may include a visual representation as follows:
   believing N=0, then:
   for each given point j from interval $[R_{1-2}+e_l, R_1-e_1]$:
      if $|(V_j-V_{j-1})>2^m$ and $|(V_j-V_{j+1})>2^m$,
      then $N=N+2^m$, m=5, ..., $j\epsilon[R_{1-2}+e_1, R_i-e_1]$
   for each given point j from interval $[R_{1-2}+e_2, R_1-e_2]$:
      if $(V_j-V_{j-1})>2^m$ and $(V_j-V_{j+1})>2^m$,
      then $N=N+2^m$, m=5 ..., 2 $j\epsilon[R_{1-2}+e_2, R_1-e_2]$
   where:
   $e_1$, $e_2$—indentations from threshold points (threshold point are empiric values equal 75 ms and 115 ms correspondently);
   $V_j$—amplitude in point j;
   N—noise level value.

18. The process as in claim 1, further comprising the step of determining whether to send a signal to the user to administer a form of external stimuli.

19. A process for analyzing a medical condition of a user comprising the following steps:
   reading at least one signal from the user;
   transferring said at: least one signal into at least one digital signal;
   extracting a plurality of parameters from said at least one digital signal;
   analyzing said plurality of parameters and comparing said plurality of parameters to a range in a set of preset parameters;
   predicting a possibility of a future occurrence of an abnormal medical condition in the user using at least one of said plurality of parameters, wherein said step of predicting a possibility of a fixture occurrence of an abnormal medical condition includes using at least one of the following parameters: Heart Rate per minute (HR) of the user; ST initial which is the ST segment level before observation beginning, ST measure which is the ST segment level at the current moment, ST threshold—which is the ST segment threshold at normal levels, QT measure—which is the QT interval duration at the current moment; QT normal which is the QT interval normal duration,
   wherein said step of predicting a possibility of a fixture occurrence of an abnormal medical condition includes using the following formula:

$$RR = 1 + \sqrt{K_1 * \left| \frac{STmeas - STinit}{STinit. + STthresh.} \right|^2 + \left| \frac{QTmeas.}{QTnorm.} - 1 \right|^2 + \left| \frac{N_1 + K_2 * N_2 + K_3 * N_3}{HR} \right|^2}$$

wherein
- $K_1$ is a first constant;
- $K_2$ is a second constant;
- $K_3$ is a third constant;
- $N_1$ is a number of single premature beats per minute;
- $N_2$ is a number of group premature beats per minute;
- $N_3$ is a number of fibrillation/flutter episodes per minute; and determining whether a user has an abnormal medical condition by determining whether said plurality of parameters fall outside of said range in said plurality of parameters and determining whether to trigger an alarm warning the user of his or her medical condition or possible future medical condition when said at least one of said plurality of parameters fall outside of said preset ranges for said preset parameters.

20. The process as in claim 19, wherein said abnormal medical condition is a development of myocardial infarction or sudden cardiac death.

21. The process as in claim 19, further comprising the step of adjusting constants $K_1$, $K_2$ and $K_3$, depending upon a set of clinical data obtained by predicting said abnormal medical condition, so that as more experiments and trials are perforated, said constants may be modified to provide more accurate forecasting.

22. The process as in claim 19, wherein initial values of said constants: $k_1$ is approximately 1.49, $K_2$ is approximately 34.91, and $k_3$ is approximately 73.68.

23. The process as in claim 19, further comprising the step of setting a range for said at least one preset parameter to predict said future occurrence of said abnormal medical condition.

24. The process as in claim 23, further comprising the step of adjusting said range for said at least one preset parameter using at least one level of adaptability.

25. The process as in claim 23, further comprising the step of adjusting said range for said at least one preset parameter using a first level, a second level and a third level of adaptability.

26. The process as in claim 25, wherein said second level includes adjusting said range based upon a log file of cardiac events wherein said adjustment is actuated by a person controlling the setting of the range.

27. The process as in claim 25, wherein said third level includes automatically adjusting said range.

28. The process as in claim 19, further comprising the steps of inputting the user's medical history into a database and storing said user's medical history.

29. The process as in claim 28, wherein said first level of adaptability includes adjusting said range based upon at least one of the following user's characteristics: age, gender, weight, or medical history.

* * * * *